US012558272B2

(12) United States Patent
Arora et al.

(10) Patent No.: US 12,558,272 B2
(45) Date of Patent: *Feb. 24, 2026

(54) SUBSTRATES AND LAMINATES FOR ABSORBENT ARTICLES

(71) Applicant: The Procter & Gamble Company, Cincinnati, OH (US)

(72) Inventors: Kelyn A. Arora, Cincinnati, OH (US); John L. Hammons, Hamilton, OH (US); Donna R. Hill, Verona, KY (US)

(73) Assignee: The Procter & Gamble Company, Cincinnati, OH (US)

( * ) Notice: Subject to any disclaimer, the term of this patent is extended or adjusted under 35 U.S.C. 154(b) by 183 days.

This patent is subject to a terminal disclaimer.

(21) Appl. No.: 18/520,860

(22) Filed: Nov. 28, 2023

(65) Prior Publication Data

US 2024/0091077 A1 Mar. 21, 2024

Related U.S. Application Data

(63) Continuation of application No. 17/005,651, filed on Aug. 28, 2020, now Pat. No. 11,864,984, which is a
(Continued)

(51) Int. Cl.
*A61F 13/513* (2006.01)
*A61F 13/511* (2006.01)
(Continued)

(52) U.S. Cl.
CPC .. *A61F 13/51305* (2013.01); *A61F 13/51104* (2013.01); *A61F 13/5116* (2013.01);
(Continued)

(58) Field of Classification Search
CPC ............ A61F 13/5116; A61F 13/51104; A61F 13/51305; A61F 13/49009;
(Continued)

(56) References Cited

U.S. PATENT DOCUMENTS

| 5,078,710 A | 1/1992 | Suda |
| 5,575,874 A | 11/1996 | Griesbach, III |

(Continued)

FOREIGN PATENT DOCUMENTS

| EP | 2159043 B1 | 6/2012 |
| IL | 197059 A | 6/2011 |

(Continued)

OTHER PUBLICATIONS

Search Report and Written Opinion for PCT/US2019/017967 dated Apr. 25, 2019, 14 pages.
(Continued)

*Primary Examiner* — Susan S Su
(74) *Attorney, Agent, or Firm* — Anna E. Haller; Amanda Herman Berghauer

(57) ABSTRACT

The present disclosure provides substrates and laminates for absorbent articles and absorbent articles comprising the substrates or laminates. The substrates and laminates may have three-dimensional elements, land areas, and increased permeability regions intermediate at least some of the land areas and at least some of the three-dimensional elements. The increased permeability regions may be positioned adjacent to the three-dimensional elements. The land areas may have a first basis weight and the increased permeability regions may have a second basis weight. The first basis weight may be greater than the second basis weight.

20 Claims, 24 Drawing Sheets

Related U.S. Application Data continuation of application No. 15/903,094, filed on Feb. 23, 2018, now Pat. No. 10,792,199.

(51) Int. Cl.

| | |
|---|---|
| *B32B 5/02* | (2006.01) |
| *B32B 5/26* | (2006.01) |
| *A61F 13/49* | (2006.01) |
| *A61F 13/514* | (2006.01) |
| *A61F 13/538* | (2006.01) |
| *B32B 5/12* | (2006.01) |
| *B32B 27/12* | (2006.01) |
| *D04H 1/54* | (2012.01) |
| *D04H 3/14* | (2012.01) |
| *D04H 3/147* | (2012.01) |

(52) U.S. Cl.

CPC ........ *B32B 5/022* (2013.01); *A61F 13/49009* (2013.01); *A61F 13/51464* (2013.01); *A61F 13/538* (2013.01); *B32B 5/12* (2013.01); *B32B 5/26* (2013.01); *B32B 27/12* (2013.01); *B32B 2262/0253* (2013.01); *B32B 2307/51* (2013.01); *D04H 1/54* (2013.01); *D04H 3/14* (2013.01); *D04H 3/147* (2013.01)

(58) Field of Classification Search

CPC .. A61F 13/51464; A61F 13/538; B32B 5/022; B32B 5/26; B32B 27/12

See application file for complete search history.

(56) References Cited

U.S. PATENT DOCUMENTS

| | | | |
|---|---|---|---|
| 7,270,861 | B2 | 9/2007 | Broering et al. |
| 7,410,683 | B2 | 8/2008 | Curro et al. |
| 7,553,532 | B2 | 6/2009 | Turner et al. |
| 7,718,243 | B2 | 5/2010 | Curro et al. |
| 7,829,173 | B2 | 11/2010 | Turner et al. |
| 8,075,977 | B2 | 12/2011 | Curro et al. |
| 8,153,225 | B2 | 4/2012 | Turner et al. |
| 8,697,218 | B2 | 4/2014 | Turner et al. |
| 10,792,199 | B2 | 10/2020 | Arora et al. |
| 2001/0055929 | A1 | 12/2001 | Zawadzki et al. |
| 2004/0131820 | A1 | 7/2004 | Turner et al. |
| 2004/0229008 | A1 | 11/2004 | Hoying |
| 2006/0019056 | A1 | 1/2006 | Turner et al. |
| 2009/0157030 | A1 | 6/2009 | Turner et al. |
| 2010/0003449 | A1 | 1/2010 | Turner et al. |
| 2010/0036339 | A1 | 2/2010 | Hammons |
| 2010/0036349 | A1 | 2/2010 | Hammons |
| 2010/0249740 | A1 | 9/2010 | Miyamoto et al. |
| 2012/0238978 | A1 | 9/2012 | Weisman et al. |
| 2012/0238982 | A1 | 9/2012 | Weisman et al. |
| 2013/0034686 | A1 | 2/2013 | Mitsuno |
| 2013/0236700 | A1 | 9/2013 | Yamanaka et al. |
| 2013/0280481 | A1 | 10/2013 | Mitsuno |
| 2014/0170367 | A1 | 6/2014 | Turner et al. |
| 2015/0250662 | A1 | 9/2015 | Isele et al. |
| 2017/0002777 | A1 | 1/2017 | Chen |
| 2017/0027774 | A1 | 2/2017 | Ashraf |
| 2017/0029993 | A1 | 2/2017 | Ashraf |
| 2017/0258650 | A1 | 9/2017 | Rosati |
| 2018/0133072 | A1 | 5/2018 | Uda et al. |
| 2018/0168893 | A1 | 6/2018 | Ashraf |
| 2018/0177643 | A1 | 6/2018 | Hao |
| 2018/0221220 | A1 | 8/2018 | Kuramochi |
| 2019/0060140 | A1 | 2/2019 | Oshima et al. |
| 2019/0117472 | A1 | 4/2019 | Erdem et al. |
| 2019/0133841 | A1 | 5/2019 | Bewick-sonntag et al. |
| 2020/0390616 | A1 | 12/2020 | Arora et al. |

FOREIGN PATENT DOCUMENTS

| | | |
|---|---|---|
| JP | 2011137249 A | 7/2011 |
| WO | 2012176656 A1 | 12/2012 |
| WO | 2013005782 A1 | 1/2013 |
| WO | 2014050310 A1 | 4/2014 |

OTHER PUBLICATIONS

All Office Actions, U.S. Appl. No. 17/005,651, filed Aug. 28, 2020.
All Office Actions; U.S. Appl. No. 15/903,094, filed Feb. 23, 2018.
Database WPI Week 201149, Thomson Scientific, London, GB; AN 2011-J05054, XP002790522, 2017, 2 pages.

SUBSTRATES AND LAMINATES FOR ABSORBENT ARTICLES

CROSS-REFERENCE TO RELATED APPLICATIONS

This application is a continuation of U.S. patent application Ser. No. 17/005,651, filed on Aug. 28, 2020, which is a continuation of U.S. patent application Ser. No. 15/903,094, filed on Feb. 23, 2018, now granted U.S. Pat. No. 10,792, 199, issued on Oct. 6, 2020, the entire disclosures of which are fully incorporated by reference herein.

FIELD OF THE INVENTION

The present disclosure is generally directed to substrates and laminates for absorbent articles and, is more specifically directed to, substrates and laminates comprising increased permeability regions for absorbent articles.

BACKGROUND

Absorbent articles are used to contain and absorb bodily exudates (i.e., urine, bowel movements, and menses). Absorbent articles may take on the form of diapers, pants, adult incontinence garments, sanitary napkins, and/or tampons, for example. These absorbent articles typically comprise a liquid permeable topsheet, a liquid impermeable backsheet, and an absorbent core positioned at least partially intermediate the topsheet and the backsheet. The absorbent articles may also comprise an acquisition layer or a secondary topsheet positioned at least partially intermediate the topsheet and the absorbent core. In recent years, consumers have shown a desire towards topsheet substrates and/or topsheet laminates, topsheet/acquisition layer laminates, or topsheet/secondary topsheet laminates that have three-dimensional elements. The substrates and/or laminates, at times, owing to their three-dimensional configuration and relatively high basis weight, may hinder bodily exudate absorbency and have a wet feeling during use. As such, these substrates and/or laminates should be improved to better wick bodily exudates therethrough.

SUMMARY

The present disclosure provides improved substrates and/or laminates for absorbent articles and absorbent articles comprising the improved substrates and/or laminates. The substrates and/or laminates may comprise three-dimensional elements having improved texture definition and/or more fibers in three-dimensional elements caused at least in part by less fiber breakage. The substrates and/or laminate may have better bodily exudate acquisition owing to increased permeability regions in the substrates and/or laminates. The substrates and/or laminates may also have a better balance of dryness and bodily exudate acquisition than previous substrates and/or laminates. Fast bodily exudate acquisition is even more important in the context of a hydrophobic wearer-facing layer. The substrates and/or laminates may employ at least one layer of a through-air bonded nonwoven material or a lightly bonded (e.g., the bonds are able to at least partially break upon application of a force or the fibers can move relative to the bonds, such as when creating three-dimensional elements) nonwoven material. The through-air bonded or lightly bonded nonwoven material may comprise carded fiber nonwoven materials or continuous fiber nonwoven material, for example. The through-air bonded, or lightly bonded, nonwoven materials may allow for fiber movement during three-dimensional element formation, thereby reducing fiber breakage and creating improved permeability regions adjacent to the three-dimensional elements. The lightly bonded materials may have calendar or point bonds that allow fibers to move out of or relative to the calendar or point bonds when one or more forces are applied to a portion of the fibers, such as during three-dimensional element formation. As such, the lightly bonded calendar or point bonds may allow for fiber movement without fiber thinning or breakage or with reduced fiber thinning or breakage. Through-air bonded nonwoven materials typically have fiber to fiber bonds and are free of calendar or point bonds. These through-air bonds are much weaker and easier to break compared to normal (i.e., not lightly bonded) calendar or point bonds. As such, during three-dimensional element formation, the through-air bonds are easily able to break and allow for fiber movement without fiber breakage or with reduced fiber breakage. This fiber movement (whether in a through-air bonded nonwoven material or a lightly bonded nonwoven material) may allow for basis weight to be lowered in areas adjacent to the three-dimensional elements to provide increased permeability regions adjacent to the three-dimensional elements. Stated another way, this fiber movement may allow for basis weight shifting in the nonwoven materials adjacent to the three-dimensional elements.

The present disclosure is directed, in part, to laminates for absorbent articles and absorbent articles comprising the laminates. The laminates may have two or more nonwoven materials, with at least one of the nonwoven materials being a through-air bonded nonwoven material. The through-air bonded nonwoven material may comprise or be composed of carded or spunbond fibers and the other layer comprise or be composed of carded or spunbond fibers. Either of the layers may comprise nano fibers or meltblown fibers, for example. The laminates may have three-dimensional elements, land areas comprising the fibers, and increased permeability regions comprising the fibers and formed adjacent to the three-dimensional elements and positioned intermediate at least some of the land areas and at least some of the three-dimensional elements. The increased permeability regions may have a lower basis weight than the land areas. A first nonwoven material may comprise normal (i.e., not lightly bonded) calendar or point bonds and a second nonwoven material may be free of normal calendar and point bonds and may only comprise fiber to fiber bonds. The second nonwoven material may also be a through-air bonded material that is free of normal calendar and point bonds. The laminates may comprise more than two nonwoven materials. The first and second nonwoven materials herein, including in the claims, may be referred to as "first" and "second" depending on which one is discussed first.

The present disclosure is directed, in part, to a substrate for an absorbent article. The substrate may comprise a nonwoven material comprising fibers. The nonwoven material may comprise a lightly bonded material having calendar or point bonds or may comprise a through-air bonded material comprising through-air bonds and being free of normal calendar or point bonds. The fibers may be spunbond fibers or carded fibers. The nonwoven material may comprise three-dimensional elements, land areas comprising the fibers and positioned in areas free of the three-dimensional elements, and increased permeability regions comprising the fiber and positioned adjacent to at least some of the three-dimensional elements. In the land areas, the nonwoven material has a first basis weight, according to the Micro-CT Test herein. In the increased permeability regions, the non-woven material has a second basis weight in the range of less than 75% to less than 25% (or other ranges herein), of the first basis weight of the land areas, according to the Micro-CT Test herein.

BRIEF DESCRIPTION OF THE DRAWINGS

The above-mentioned and other features and advantages of the present disclosure, and the manner of attaining them, will become more apparent and the disclosure itself will be better understood by reference to the following description of example forms of the disclosure taken in conjunction with the accompanying drawings, wherein.

DETAILED DESCRIPTION

Various non-limiting forms of the present disclosure will now be described to provide an overall understanding of the principles of the structure, function, manufacture, and use of the substrates and laminates for absorbent articles disclosed herein. One or more examples of these non-limiting forms are illustrated in the accompanying drawings. Those of ordinary skill in the art will understand that the substrates and laminates for absorbent articles described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

Initially, a general description of example absorbent articles will be provided and then the substrates and/or laminates for absorbent articles or other consumer products will be discussed. The substrates (i.e., single layer) for absorbent articles may form a topsheet, an acquisition layer, a distribution layer, a secondary topsheet, a core cover, other suitable layer, or a substrate in a consumer products other than absorbent articles. The laminates (i.e., more than one layer) for absorbent articles may form a topsheet laminate, a topsheet/acquisition layer laminate, a top sheet/secondary topsheet laminate, an outer cover nonwoven material laminate, another laminate for other components of absorbent articles, or laminates for consumer products other than absorbent articles, for example.

General Description of an Absorbent Article

Figure 1:
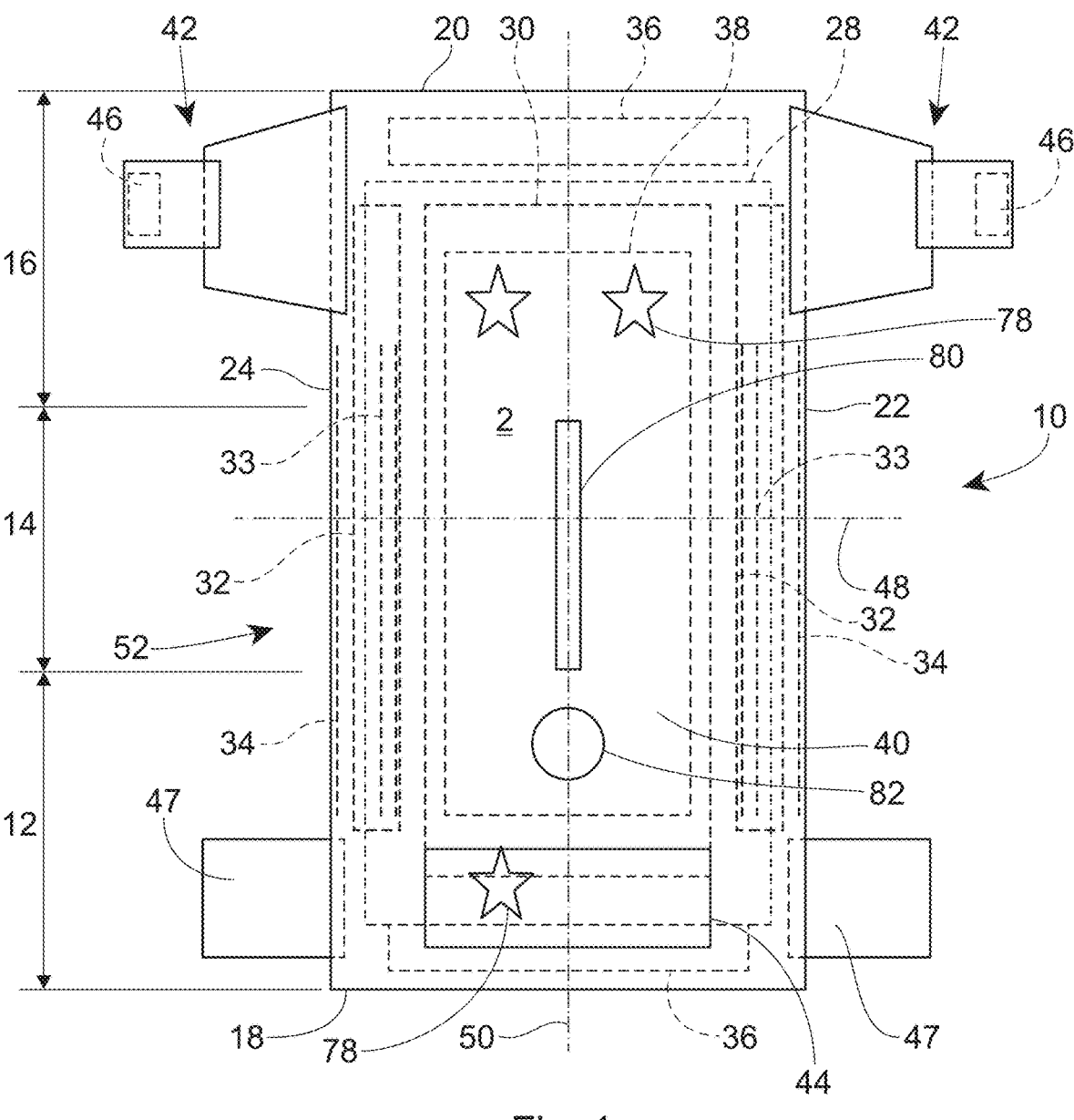
FIG. 1 is a plan view of an example absorbent article in the form of a taped diaper, garment-facing surface facing the viewer, in a flat laid-out state.
Figure 2:
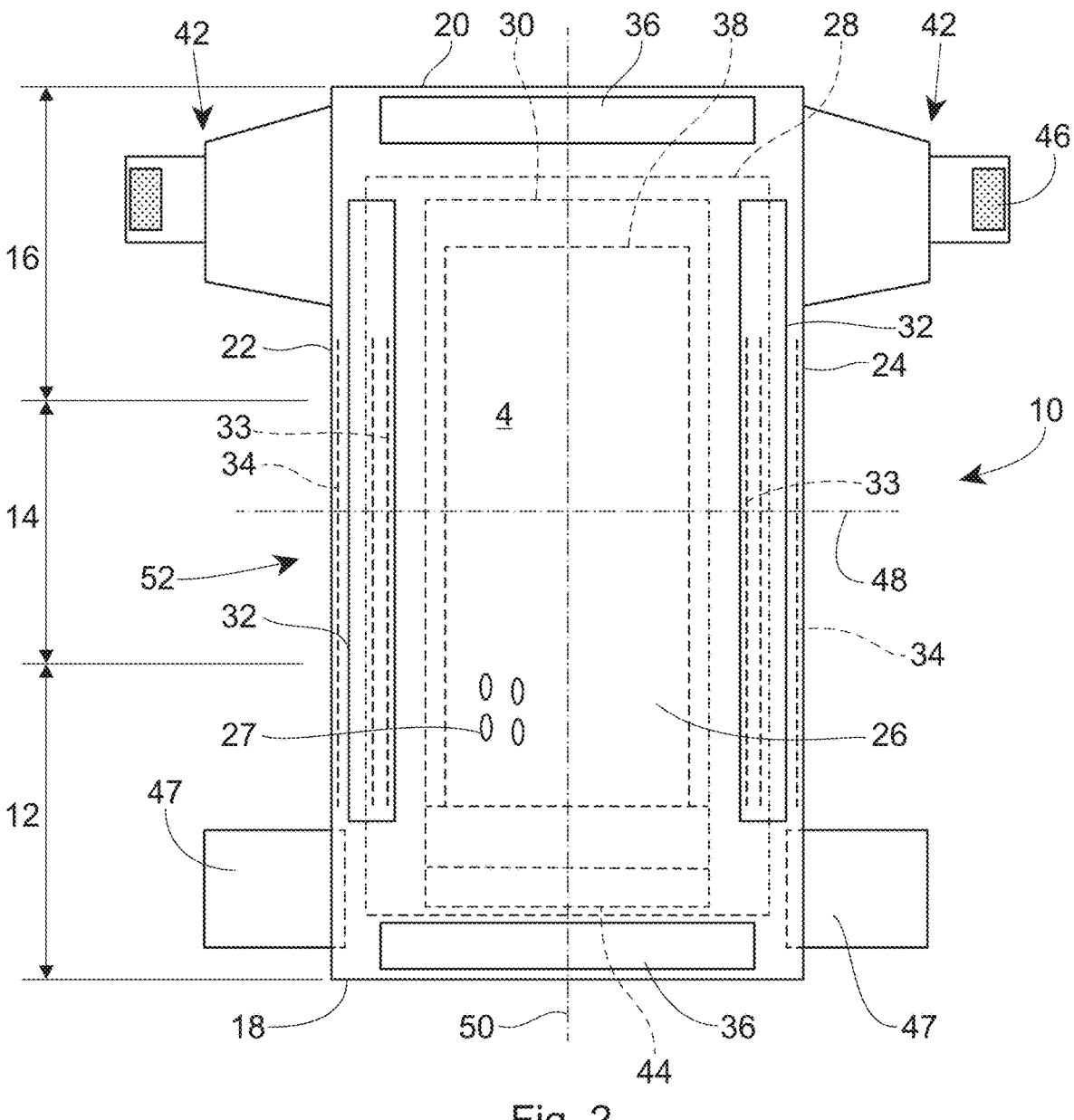
FIG. 2 is a plan view of the example absorbent article of FIG. 1, wearer-facing surface facing the viewer, in a flat laid-out state.
Figure 3:
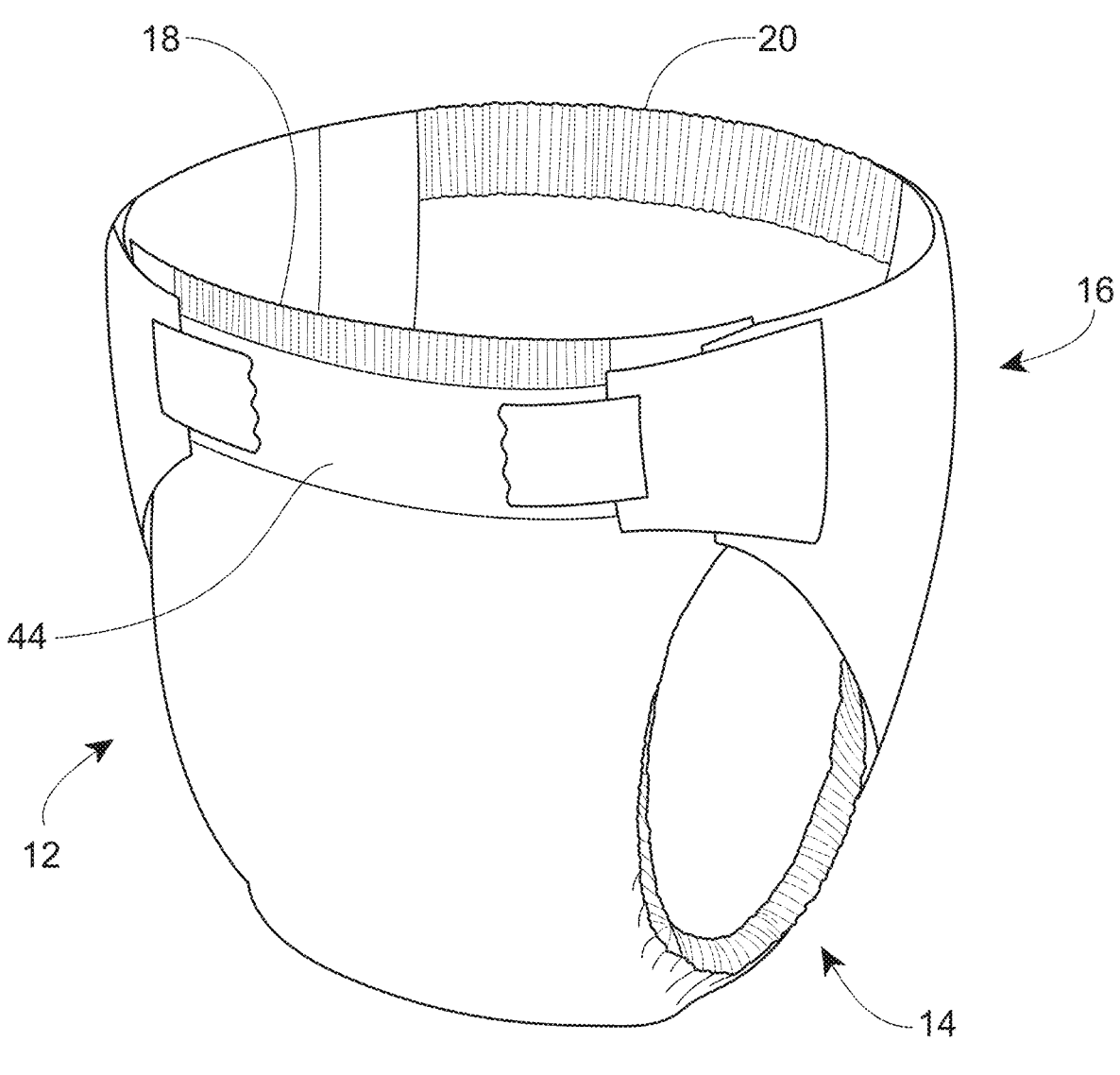
FIG. 3 is a front perspective view of the absorbent article of FIGS. 1 and 2 in a fastened position.

An example absorbent article 10 according to the present disclosure, shown in the form of a taped diaper, is represented in FIGS. 1-3. FIG. 1 is a plan view of the example absorbent article 10, garment-facing surface 2 facing the viewer in a flat, laid-out state (i.e., no elastic contraction). FIG. 2 is a plan view of the example absorbent article 10 of FIG. 1, wearer-facing surface 4 facing the viewer in a flat, laid-out state. FIG. 3 is a front perspective view of the absorbent article 10 of FIGS. 1 and 2 in a fastened configuration. The absorbent article 10 of FIGS. 1-3 is shown for illustration purposes only as the present disclosure may be used for making a wide variety of diapers, including adult incontinence products, pants, or other absorbent articles, such as sanitary napkins and absorbent pads, for example.

The absorbent article 10 may comprise a front waist region 12, a crotch region 14, and a back waist region 16. The crotch region 14 may extend intermediate the front waist region 12 and the back waist region 16. The front wait region 12, the crotch region 14, and the back waist region 16 may each be ⅓ of the length of the absorbent article 10. The absorbent article 10 may comprise a front end edge 18, a back end edge 20 opposite to the front end edge 18, and longitudinally extending, transversely opposed side edges 22 and 24 defined by the chassis 52.

The absorbent article 10 may comprise a liquid permeable topsheet 26, a liquid impermeable backsheet 28, and an absorbent core 30 positioned at least partially intermediate the topsheet 26 and the backsheet 28. The absorbent article 10 may also comprise one or more pairs of barrier leg cuffs 32 with or without elastics 33, one or more pairs of leg elastics 34, one or more elastic waistbands 36, and/or one or more acquisition materials 38. The acquisition material or materials 38 may be positioned intermediate the topsheet 26 and the absorbent core 30. An outer cover material 40, such as a nonwoven material, may cover a garment-facing side of the backsheet 28. The absorbent article 10 may comprise back ears 42 in the back waist region 16. The back ears 42 may comprise fasteners 46 and may extend from the back waist region 16 of the absorbent article 10 and attach (using the fasteners 46) to the landing zone area or landing zone material 44 on a garment-facing portion of the front waist region 12 of the absorbent article 10. The absorbent article 10 may also have front ears 47 in the front waist region 12. The absorbent article 10 may have a central lateral (or transverse) axis 48 and a central longitudinal axis 50. The central lateral axis 48 extends perpendicular to the central longitudinal axis 50.

Figure 4:
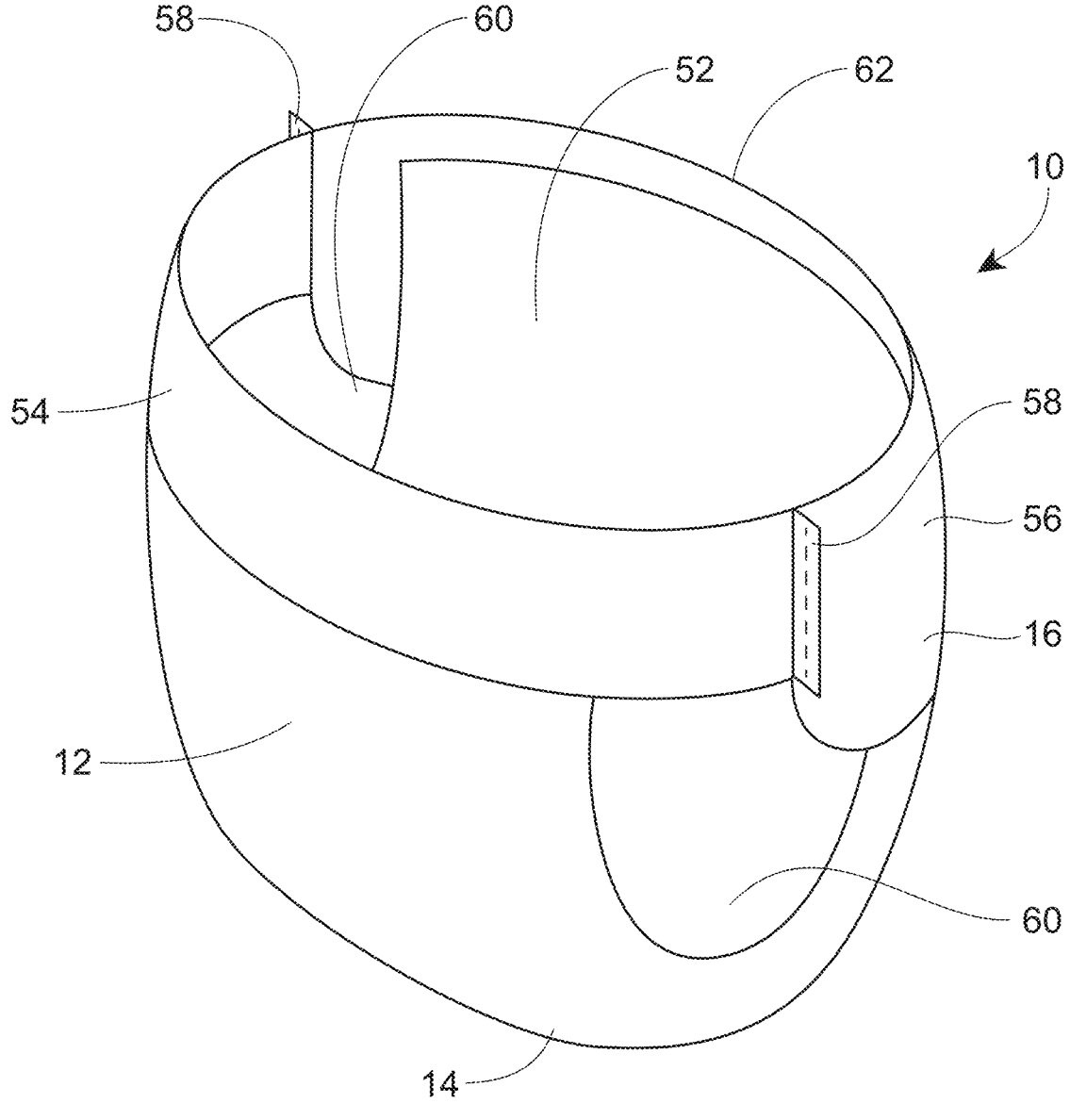
FIG. 4 is a front perspective view of an absorbent article in the form of a pant.
Figure 5:
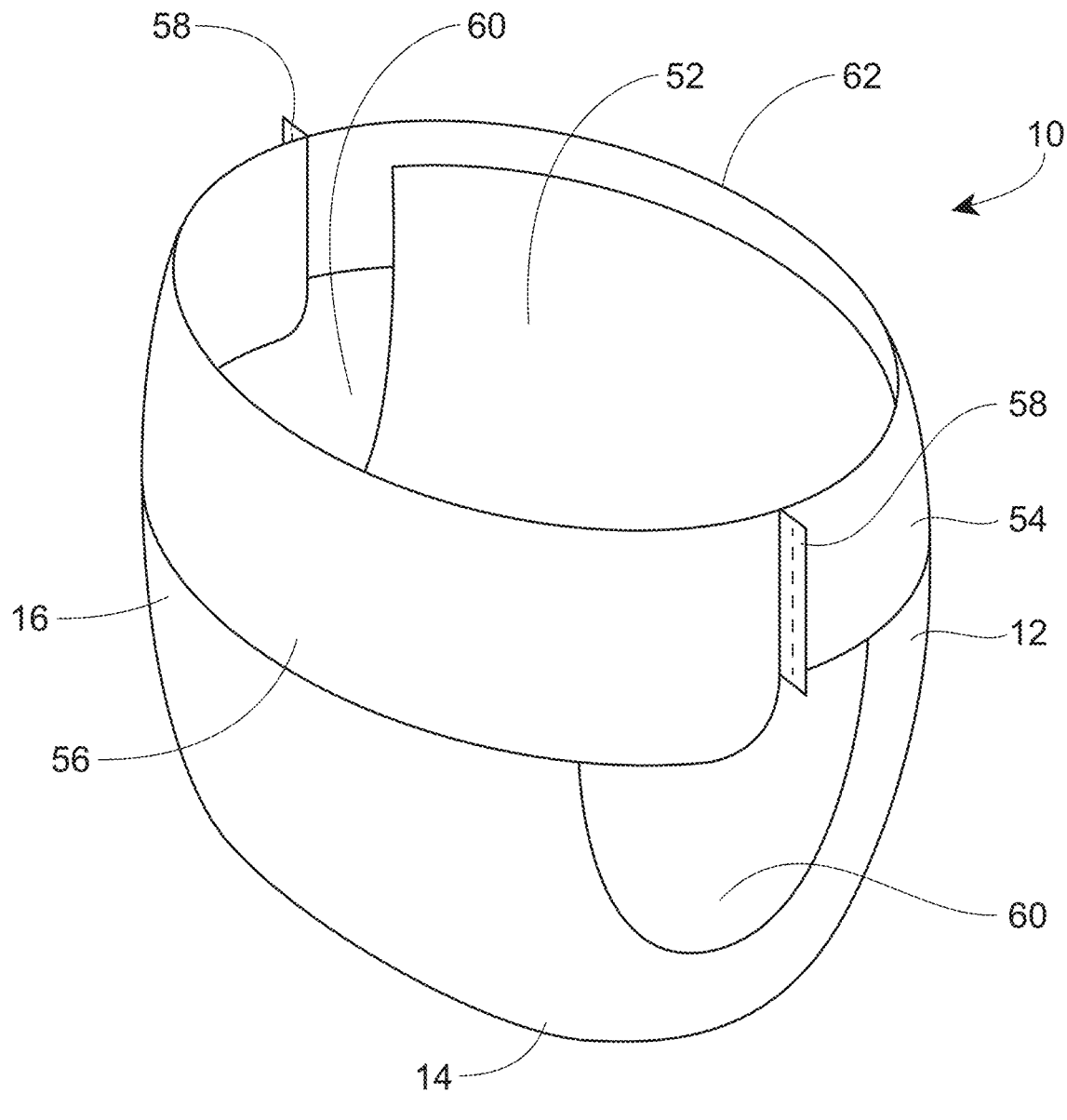
FIG. 5 is a rear perspective view of the absorbent article of FIG. 4.
Figure 6:
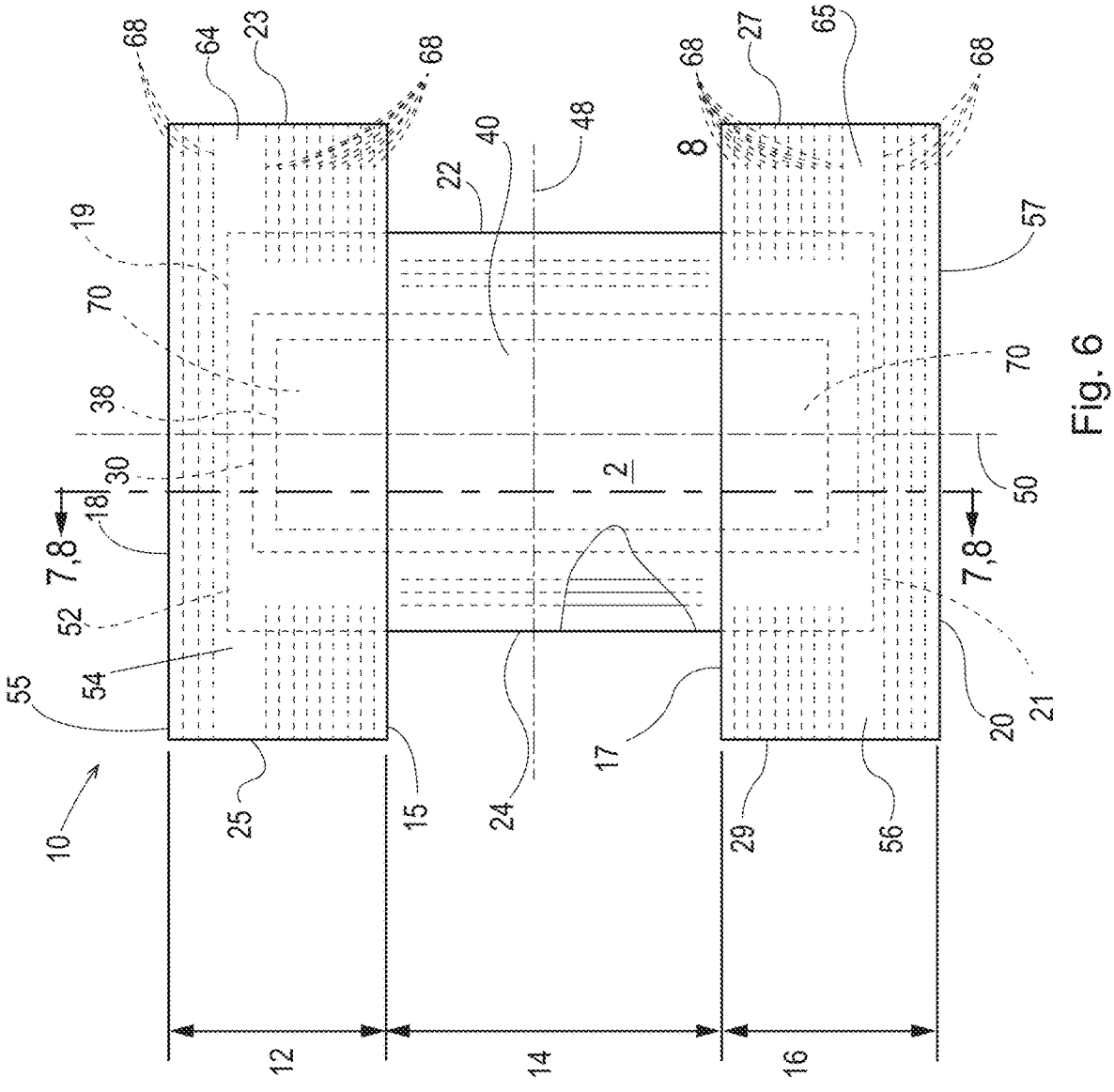
FIG. 6 is a plan view of the absorbent article of FIG. 4, laid flat, with a garment-facing surface facing the viewer.
Figure 7:
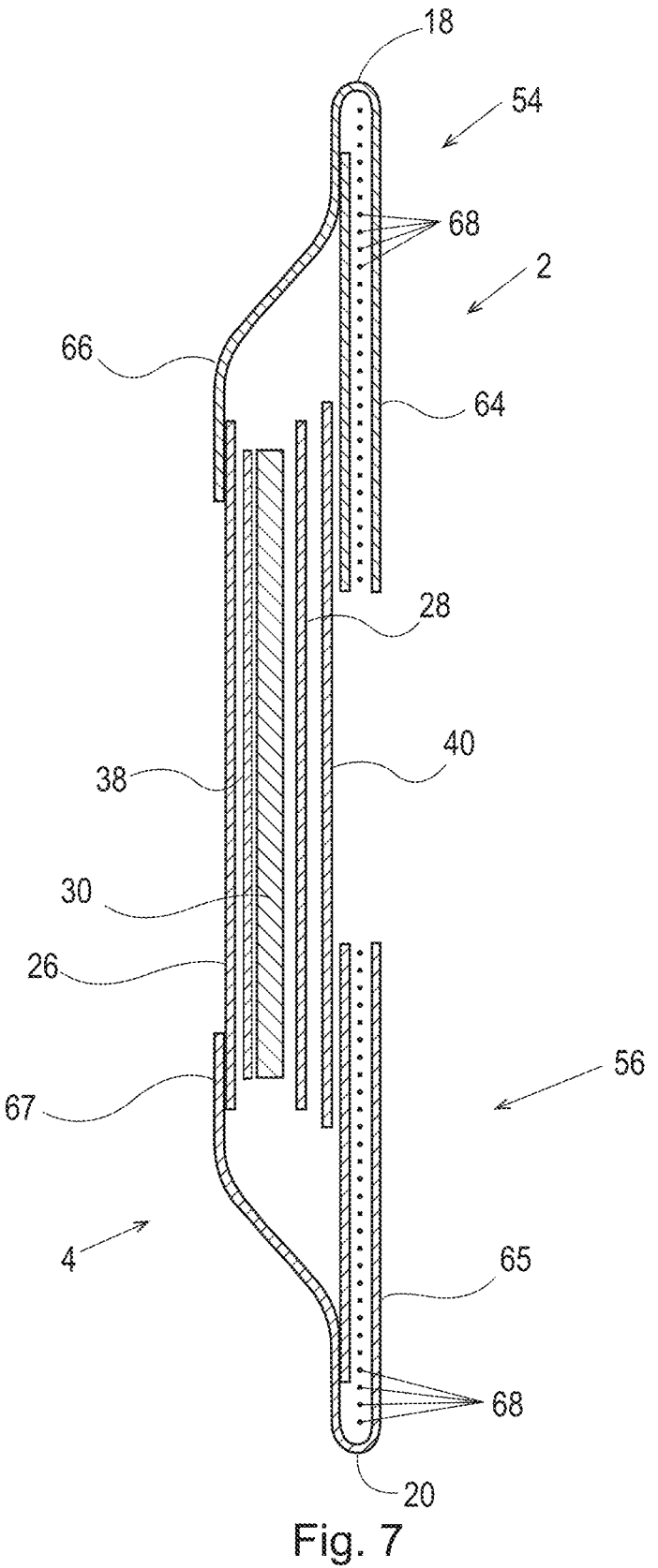
FIG. 7 is a cross-sectional view of the absorbent article taken about line 7-7 of FIG. 6.
Figure 8:
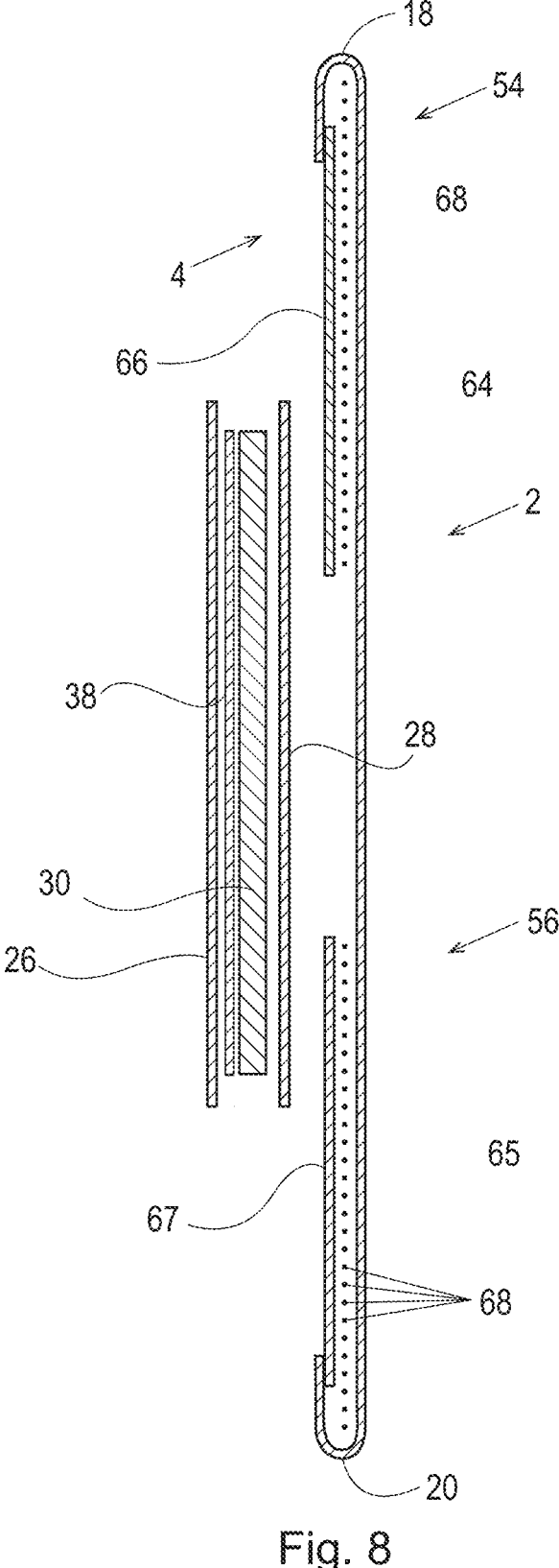
FIG. 8 is a cross-sectional view of the absorbent article taken about line 8-8 of FIG. 6.

In other instances, the absorbent article may be in the form of a pant having permanent or refastenable side seams. Suitable refastenable seams are disclosed in U.S. Pat. Appl. Pub. No. 2014/0005020 and U.S. Pat. No. 9,421,137. Referring to FIGS. 4-8, an example absorbent article 10 in the form of a pant is illustrated. FIG. 4 is a front perspective view of the absorbent article 10. FIG. 5 is a rear perspective view of the absorbent article 10. FIG. 6 is a plan view of the absorbent article 10, laid flat, with the garment-facing surface facing the viewer. Elements of FIG. 4-8 having the same reference number as described above with respect to FIGS. 1-3 may be the same element (e.g., absorbent core 30). FIG. 7 is an example cross-sectional view of the absorbent article taken about line 7-7 of FIG. 6. FIG. 8 is an example cross-sectional view of the absorbent article taken about line 8-8 of FIG. 6. FIGS. 7 and 8 illustrate example forms of front and back belts 54, 56. The absorbent article 10 may have a front waist region 12, a crotch region 14, and a back waist region 16. Each of the regions 12, 14, and 16 may be ⅓ of the length of the absorbent article 10. The absorbent article 10 may have a chassis 52 (sometimes referred to as a central chassis or central panel) comprising a topsheet 26, a backsheet 28, and an absorbent core 30 disposed at least partially intermediate the topsheet 26 and the backsheet 28, and an optional acquisition material 38, similar to that as described above with respect to FIGS. 1-3. The absorbent article 10 may comprise a front belt 54 in the front waist region 12 and a back belt 56 in the back waist region 16. The chassis 52 may be joined to a wearer-facing surface 4 of the front and back belts 54, 56 or to a garment-facing surface 2 of the belts 54, 56. Side edges 23 and 25 of the front belt 54 may be joined to side edges 27 and 29, respectively, of the back belt 56 to form two side seams 58. The side seams 58 may be any suitable seams known to those of skill in the art, such as butt seams or overlap seams, for example. When the side seams 58 are permanently formed or refastenably closed, the absorbent article 10 in the form of a pant has two leg openings 60 and a waist opening circumference 62. The side seams 58 may be permanently joined using adhesives or bonds, for example, or may be refastenably closed using hook and loop fasteners, for example.

Belts

Referring to FIGS. 7 and 8, the front and back belts 54 and 56 may comprise front and back inner belt layers 66 and 67 and front and back outer belt layers 64 and 65 having an elastomeric material (e.g., strands 68 or a film (which may be apertured)) disposed at least partially therebetween. The elastic elements 68 or the film may be relaxed (including being cut) to reduce elastic strain over the absorbent core 30 or, may alternatively, run continuously across the absorbent core 30. The elastics elements 68 may have uniform or variable spacing therebetween in any portion of the belts. The elastic elements 68 may also be pre-strained the same amount or different amounts. The front and/or back belts 54 and 56 may have one or more elastic element free zones 70 where the chassis 52 overlaps the belts 54, 56. In other instances, at least some of the elastic elements 68 may extend continuously across the chassis 52.

The front and back inner belt layers 66, 67 and the front and back outer belt layers 64, 65 may be joined using adhesives, heat bonds, pressure bonds or thermoplastic bonds. Various suitable belt layer configurations can be found in U.S. Pat. Appl. Pub. No. 2013/0211363.

Front and back belt end edges 55 and 57 may extend longitudinally beyond the front and back chassis end edges 19 and 21 (as shown in FIG. 6) or they may be co-terminus. The front and back belt side edges 23, 25, 27, and 29 may extend laterally beyond the chassis side edges 22 and 24. The front and back belts 54 and 56 may be continuous (i.e., having at least one layer that is continuous) from belt side edge to belt side edge (e.g., the transverse distances from 23 to 25 and from 27 to 29). Alternatively, the front and back belts 54 and 56 may be discontinuous from belt side edge to belt side edge (e.g., the transverse distances from 23 to 25 and 27 to 29), such that they are discrete.

As disclosed in U.S. Pat. No. 7,901,393, the longitudinal length (along the central longitudinal axis 50) of the back belt 56 may be greater than the longitudinal length of the front belt 54, and this may be particularly useful for increased buttocks coverage when the back belt 56 has a greater longitudinal length versus the front belt 54 adjacent to or immediately adjacent to the side seams 58.

The front outer belt layer 64 and the back outer belt layer 65 may be separated from each other, such that the layers are discrete or, alternatively, these layers may be continuous, such that a layer runs continuously from the front belt end edge 55 to the back belt end edge 57. This may also be true for the front and back inner belt layers 66 and 67—that is, they may also be longitudinally discrete or continuous. Further, the front and back outer belt layers 64 and 65 may be longitudinally continuous while the front and back inner belt layers 66 and 67 are longitudinally discrete, such that a gap is formed between them—a gap between the front and back inner and outer belt layers 64, 65, 66, and 67 is shown in FIG. 7 and a gap between the front and back inner belt layers 66 and 67 is shown in FIG. 8.

The front and back belts 54 and 56 may include slits, holes, and/or perforations providing increased breathability, softness, and a garment-like texture. Underwear-like appearance can be enhanced by substantially aligning the waist and leg edges at the side seams 58 (see FIGS. 4 and 5).

The front and back belts 54 and 56 may comprise graphics (see e.g., 78 of FIG. 1). The graphics may extend substantially around the entire circumference of the absorbent article 10 and may be disposed across side seams 58 and/or across proximal front and back belt seams 15 and 17; or, alternatively, adjacent to the seams 58, 15, and 17 in the manner described in U.S. Pat. No. 9,498,389 to create a more underwear-like article. The graphics may also be discontinuous.

Alternatively, instead of attaching belts 54 and 56 to the chassis 52 to form a pant, discrete side panels may be attached to side edges of the chassis 22 and 24. Suitable forms of pants comprising discrete side panels are disclosed in U.S. Pat. Nos. 6,645,190; 8,747,379; 8,372,052; 8,361, 048; 6,761,711; 6,817,994; 8,007,485; 7,862,550; 6,969, 377; 7,497,851; 6,849,067; 6,893,426; 6,953,452; 6,840, 928; 8,579,876; 7,682,349; 7,156,833; and 7,201,744.

Topsheet

The topsheet 26 is the part of the absorbent article 10 that is in contact with the wearer's skin. The topsheet 26 may be joined to portions of the backsheet 28, the absorbent core 30, the barrier leg cuffs 32, and/or any other layers as is known to those of ordinary skill in the art. The topsheet 26 may be compliant, soft-feeling, and non-irritating to the wearer's skin. Further, at least a portion of, or all of, the topsheet may be liquid permeable, permitting liquid bodily exudates to readily penetrate through its thickness. A suitable topsheet may be manufactured from continuous fibers (e.g., spunbond), carded fibers, cotton fibers, other natural fibers, for example. The topsheet may comprise through-air bonded nonwoven materials, through-air bonded nonwoven materials and calendar bonded nonwoven materials, as will be discussed further below. The topsheet may have one or more layers and be a laminate (as discussed below). Some topsheet are apertured (FIG. 2, element 27). Any portion of the topsheet may be coated with a skin care composition, an antibacterial agent, a surfactant, and/or other beneficial agents. The topsheet may be hydrophilic or hydrophobic or may have hydrophilic and/or hydrophobic portions or layers. If the topsheet is hydrophobic, in some instances, apertures may be present so that bodily exudates may pass through the topsheet.

The topsheet may be one of the example laminates discussed below or may form a portion of the laminate in combination with an acquisition material or layer, a secondary topsheet, or another layer or material, for example.

Backsheet

The backsheet 28 is generally that portion of the absorbent article 10 positioned proximate to the garment-facing surface of the absorbent core 30. The backsheet 28 may be joined to portions of the topsheet 26, the outer cover material 40, the absorbent core 30, and/or any other layers of the absorbent article by any attachment methods known to those of skill in the art. The backsheet 28 prevents, or at least inhibits, the bodily exudates absorbed and contained in the absorbent core 10 from soiling articles such as bedsheets, undergarments, and/or clothing. The backsheet is typically liquid impermeable, or at least substantially liquid impermeable. The backsheet may, for example, be or comprise a thin plastic film, such as a thermoplastic film having a thickness of about 0.012 mm to about 0.051 mm. Other suitable backsheet materials may include breathable materials which permit vapors to escape from the absorbent article, while still preventing, or at least inhibiting, bodily exudates from passing through the backsheet.

Outer Cover Material

The outer cover material (sometimes referred to as a backsheet nonwoven) 40 may comprise one or more nonwoven materials joined to the backsheet 28 and that covers the backsheet 28. The outer cover material 40 forms at least a portion of the garment-facing surface 2 of the absorbent article 10 and effectively "covers" the backsheet 28 so that film is not present on the garment-facing surface 2. The outer cover material 40 may comprise a bond pattern, apertures, and/or three-dimensional elements. The outer cover material may comprise the laminates discussed herein.

Absorbent Core

Figure 9:
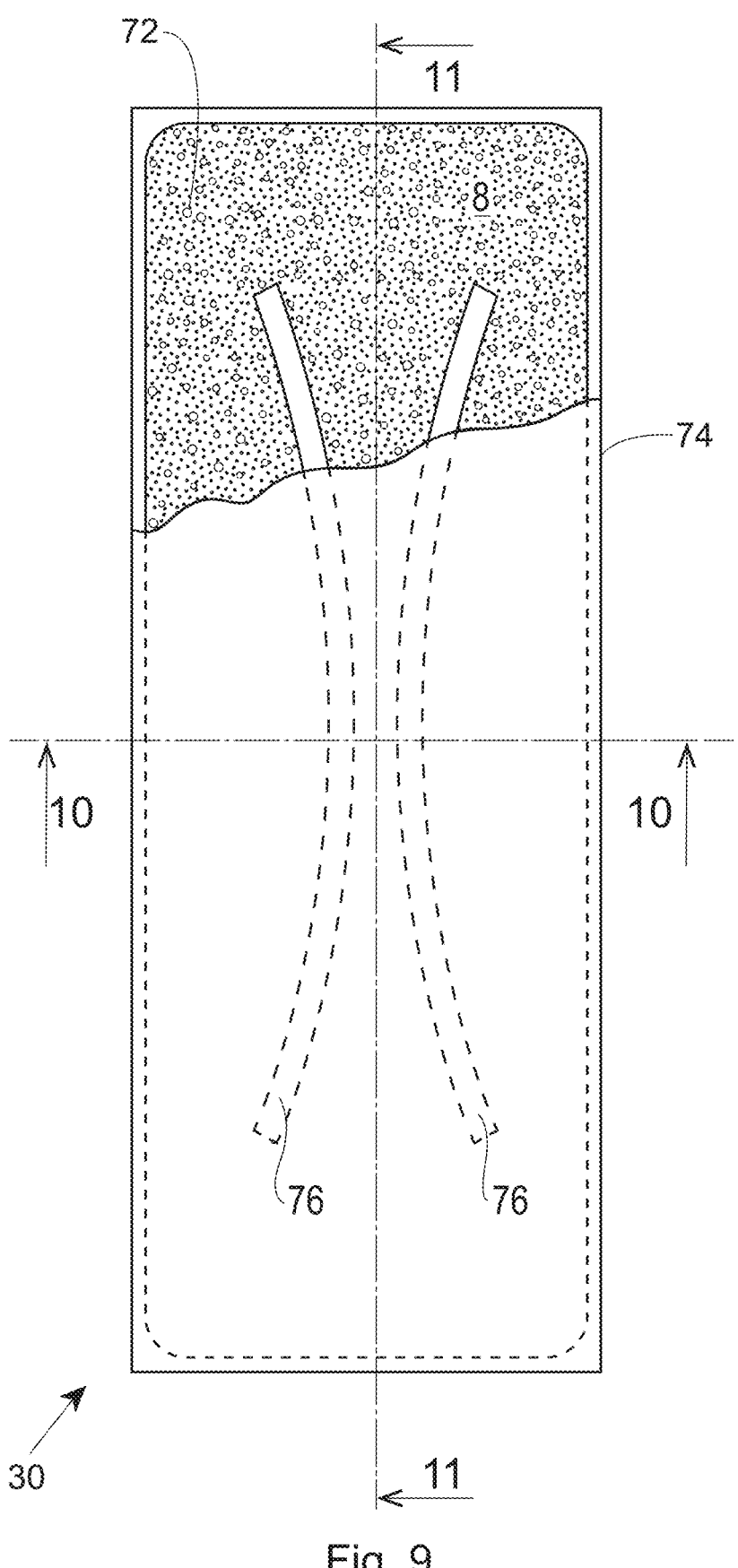
FIG. 9 is a plan view of an example absorbent core or an absorbent article.
Figure 10:
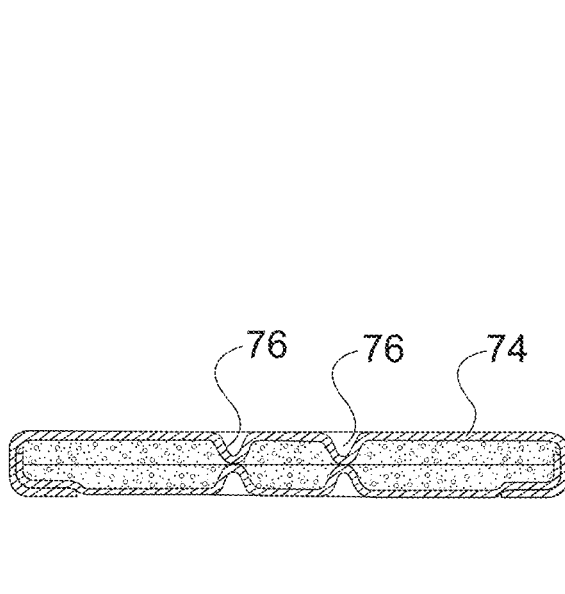
FIG. 10 is a cross-sectional view, taken about line 10-10, of the absorbent core of FIG. 9.
Figure 11:
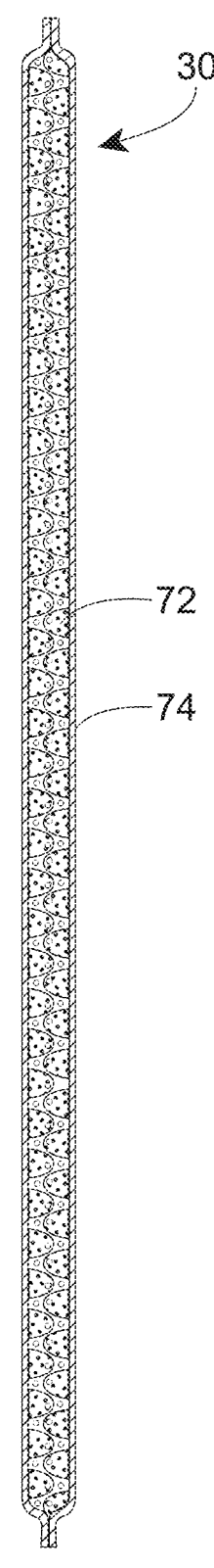
FIG. 11 is a cross-sectional view, taken about line 11-11, of the absorbent core of FIG. 10.

As used herein, the term "absorbent core" 30 refers to the component of the absorbent article 10 having the most absorbent capacity and that comprises an absorbent material. Referring to FIGS. 9-11, in some instances, absorbent material 72 may be positioned within a core bag or a core wrap 74. The absorbent material may be profiled or not profiled, depending on the specific absorbent article. The absorbent core 30 may comprise, consist essentially of, or consist of, a core wrap, absorbent material 72, and glue enclosed within the core wrap. The absorbent material may comprise superabsorbent polymers, a mixture of superabsorbent polymers and air felt, only air felt, and/or a high internal phase emulsion foam. In some instances, the absorbent material may comprise at least 80%, at least 85%, at least 90%, at least 95%, at least 99%, or up to 100% superabsorbent polymers, by weight of the absorbent material. In such instances, the absorbent material may free of air felt, or at least mostly free of air felt. The absorbent core periphery, which may be the periphery of the core wrap, may define any suitable shape, such as rectangular "T," "Y," "hour-glass," or "dog-bone" shaped, for example. An absorbent core periphery having a generally "dog bone" or "hour-glass" shape may taper along its width towards the crotch region 14 of the absorbent article 10.

Referring to FIGS. 9-11, the absorbent core 30 may have areas having little or no absorbent material 72, where a wearer-facing surface of the core bag 74 may be joined to a garment-facing surface of the core bag 74. These areas having little or no absorbent material may be referred to as "channels" 76. These channels can embody any suitable shapes and any suitable number of channels may be provided. In other instances, the absorbent core may be embossed to create the impression of channels. The absorbent core in FIGS. 9-11 is merely an example absorbent core. Many other absorbent cores with or without channels are also within the scope of the present disclosure.

Barrier Leg Cuffs/Leg Elastics

Referring to FIGS. 1 and 2, for example, the absorbent article 10 may comprise one or more pairs of barrier leg cuffs 32 and one or more pairs of leg elastics 34. The barrier leg cuffs 32 may be positioned laterally inboard of leg elastics 34. Each barrier leg cuff 32 may be formed by a piece of material which is bonded to the absorbent article 10 so it can extend upwards from a wearer-facing surface 4 of the absorbent article 10 and provide improved containment of body exudates approximately at the junction of the torso and legs of the wearer. The barrier leg cuffs 32 are delimited by a proximal edge joined directly or indirectly to the topsheet and/or the backsheet and a free terminal edge, which is intended to contact and form a seal with the wearer's skin. The barrier leg cuffs 32 may extend at least partially between the front end edge 18 and the back end edge 20 of the absorbent article 10 on opposite sides of the central longitudinal axis 50 and may be at least present in the crotch region 14. The barrier leg cuffs 32 may each comprise one or more elastics 33 (e.g., elastic strands or strips) near or at the free terminal edge. These elastics 33 cause the barrier leg cuffs 32 to help form a seal around the legs and torso of a wearer. The leg elastics 34 extend at least partially between the front end edge 18 and the back end edge 20. The leg elastics 34 essentially cause portions of the absorbent article 10 proximate to the chassis side edges 22, 24 to help form a seal around the legs of the wearer. The leg elastics 34 may extend at least within the crotch region 14.

Elastic Waistband

Referring to FIGS. 1 and 2, the absorbent article 10 may comprise one or more elastic waistbands 36. The elastic waistbands 36 may be positioned on the garment-facing surface 2 or the wearer-facing surface 4. As an example, a first elastic waistband 36 may be present in the front waist region 12 near the front belt end edge 18 and a second elastic waistband 36 may be present in the back waist region 16 near the back end edge 20. The elastic waistbands 36 may aid in sealing the absorbent article 10 around a waist of a wearer and at least inhibiting bodily exudates from escaping the absorbent article 10 through the waist opening circumference. In some instances, an elastic waistband may fully surround the waist opening circumference of an absorbent article.

Acquisition Materials

Referring to FIGS. 1, 2, 7, and 8, one or more acquisition materials 38 may be present at least partially intermediate the topsheet 26 and the absorbent core 30. The acquisition materials 38 are typically hydrophilic materials that provide significant wicking of bodily exudates. These materials may dewater the topsheet 26 and quickly move bodily exudates into the absorbent core 30. The acquisition materials 38 may comprise one or more nonwoven materials, foams, cellulosic materials, cross-linked cellulosic materials, air laid cellulosic nonwoven materials, spunlace materials, or combinations thereof, for example. In some instances, portions of the acquisition materials 38 may extend through portions of the topsheet 26, portions of the topsheet 26 may extend through portions of the acquisition materials 38, and/or the topsheet 26 may be nested with the acquisition materials 38. Typically, an acquisition material 38 may have a width and length that are smaller than the width and length of the topsheet 26. The acquisition material may be a secondary topsheet in the feminine pad context. The acquisition material may have one or more channels as described above with reference to the absorbent core 30 (including the embossed version). The channels in the acquisition material may align or not align with channels in the absorbent core 30. In an example, a first acquisition material may comprise a nonwoven material and as second acquisition material may comprise a cross-linked cellulosic material.

In the context of the laminates discussed herein, the acquisition materials may be combined with a topsheet to form the laminates.

Landing Zone

Referring to FIGS. 1 and 2, the absorbent article 10 may have a landing zone area 44 that is formed in a portion of the garment-facing surface 2 of the outer cover material 40. The landing zone area 44 may be in the back waist region 16 if the absorbent article 10 fastens from front to back or may be in the front waist region 12 if the absorbent article 10 fastens back to front. In some instances, the landing zone 44 may be or may comprise one or more discrete nonwoven materials that are attached to a portion of the outer cover material 40 in the front waist region 12 or the back waist region 16 depending upon whether the absorbent article fastens in the front or the back. In essence, the landing zone 44 is configured to receive the fasteners 46 and may comprise, for example, a plurality of loops configured to be engaged with, a plurality of hooks on the fasteners 46, or vice versa.

Wetness Indicator/Graphics

Referring to FIG. 1, the absorbent articles 10 of the present disclosure may comprise graphics 78 and/or wetness indicators 80 that are visible from the garment-facing surface 2. The graphics 78 may be printed on the landing zone 40, the backsheet 28, and/or at other locations. The wetness indicators 80 are typically applied to the absorbent core facing side of the backsheet 28, so that they can be contacted by bodily exudates within the absorbent core 30. In some instances, the wetness indicators 80 may form portions of the graphics 78. For example, a wetness indicator may appear or disappear and create/remove a character within some graphics. In other instances, the wetness indicators 80 may coordinate (e.g., same design, same pattern, same color) or not coordinate with the graphics 78.

Front and Back Ears

Referring to FIGS. 1 and 2, as referenced above, the absorbent article 10 may have front and/or back ears 47, 42 in a taped diaper context. Only one set of ears may be required in most taped diapers. The single set of ears may comprise fasteners 46 configured to engage the landing zone or landing zone area 44. If two sets of ears are provided, in most instances, only one set of the ears may have fasteners 46, with the other set being free of fasteners. The ears, or portions thereof, may be elastic or may have elastic panels. In an example, an elastic film or elastic strands may be positioned intermediate a first nonwoven material and a second nonwoven material. The elastic film may or may not be apertured. The ears may be shaped. The ears may be integral (e.g., extension of the outer cover material 40, the backsheet 28, and/or the topsheet 26) or may be discrete components attached to a chassis 52 of the absorbent article on a wearer-facing surface 4, on the garment-facing surface 2, or intermediate the two surfaces 4, 2.

Sensors

Referring again to FIG. 1, the absorbent articles of the present disclosure may comprise a sensor system 82 for monitoring changes within the absorbent article 10. The sensor system 82 may be discrete from or integral with the absorbent article 10. The absorbent article 10 may comprise sensors that can sense various aspects of the absorbent article 10 associated with insults of bodily exudates such as urine and/or BM (e.g., the sensor system 82 may sense variations in temperature, humidity, presence of ammonia or urea, various vapor components of the exudates (urine and feces), changes in moisture vapor transmission through the absorbent articles garment-facing layer, changes in translucence of the garment-facing layer, and/or color changes through the garment-facing layer). Additionally, the sensor system 82 may sense components of urine, such as ammonia or urea and/or byproducts resulting from reactions of these components with the absorbent article 10. The sensor system 82 may sense byproducts that are produced when urine mixes with other components of the absorbent article 10 (e.g., adhesives, agm). The components or byproducts being sensed may be present as vapors that may pass through the garment-facing layer. It may also be desirable to place reactants in the absorbent article that change state (e.g. color, temperature) or create a measurable byproduct when mixed with urine or BM. The sensor system 82 may also sense changes in pH, pressure, odor, the presence of gas, blood, a chemical marker or a biological marker or combinations thereof. The sensor system 82 may have a component on or proximate to the absorbent article that transmits a signal to a receiver more distal from the absorbent article, such as an iPhone, for example. The receiver may output a result to communicate to the caregiver a condition of the absorbent article 10. In other instances, a receiver may not be provided, but instead the condition of the absorbent article 10 may be visually or audibly apparent from the sensor on the absorbent article.

Packages

The absorbent articles of the present disclosure may be placed into packages. The packages may comprise polymeric films and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages.

Sanitary Napkin

Figure 12:
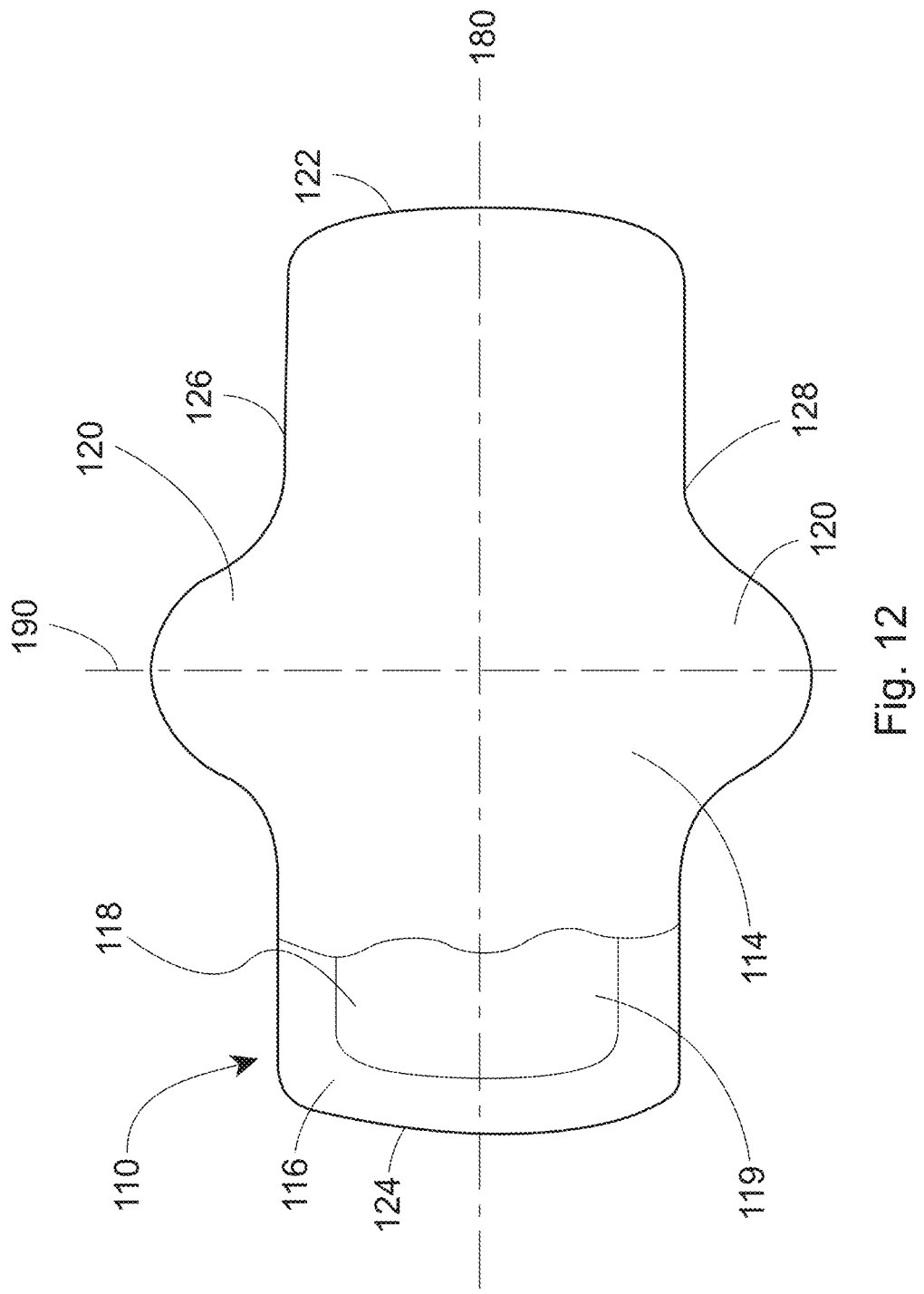
FIG. 12 is a plan view of an example absorbent article of the present disclosure that is a sanitary napkin.

Referring to FIG. 12, an absorbent article of the present disclosure may be a sanitary napkin 110. The sanitary napkin 110 may comprise a liquid permeable topsheet 114, a liquid impermeable, or substantially liquid impermeable, backsheet 116, and an absorbent core 118. The liquid impermeable backsheet 116 may or may not be vapor permeable. The absorbent core 118 may have any or all of the features described herein with respect to the absorbent core 30 and, in some forms, may have a secondary topsheet 119 (STS) instead of the acquisition materials disclosed above. The STS 119 may comprise one or more channels, as described above (including the embossed version). In some forms, channels in the STS 119 may be aligned with channels in the absorbent core 118. The sanitary napkin 110 may also comprise wings 120 extending outwardly with respect to a longitudinal axis 180 of the sanitary napkin 110. The sanitary napkin 110 may also comprise a lateral axis 190. The wings 120 may be joined to the topsheet 114, the backsheet 116, and/or the absorbent core 118. The sanitary napkin 110 may also comprise a front edge 122, a back edge 124 longitudinally opposing the front edge 122, a first side edge 126, and a second side edge 128 longitudinally opposing the first side edge 126. The longitudinal axis 180 may extend from a midpoint of the front edge 122 to a midpoint of the back edge 124. The lateral axis 190 may extend from a midpoint of the first side edge 128 to a midpoint of the second side edge 128. The sanitary napkin 110 may also be provided with additional features commonly found in sanitary napkins as is known in the art.

The secondary topsheet may be combined with a topsheet to form the laminates discussed herein. In other instances, the laminates discussed herein may only form the topsheet of a sanitary napkin.

Examples Cross-Sectional Views of Absorbent Articles

Figure 13:
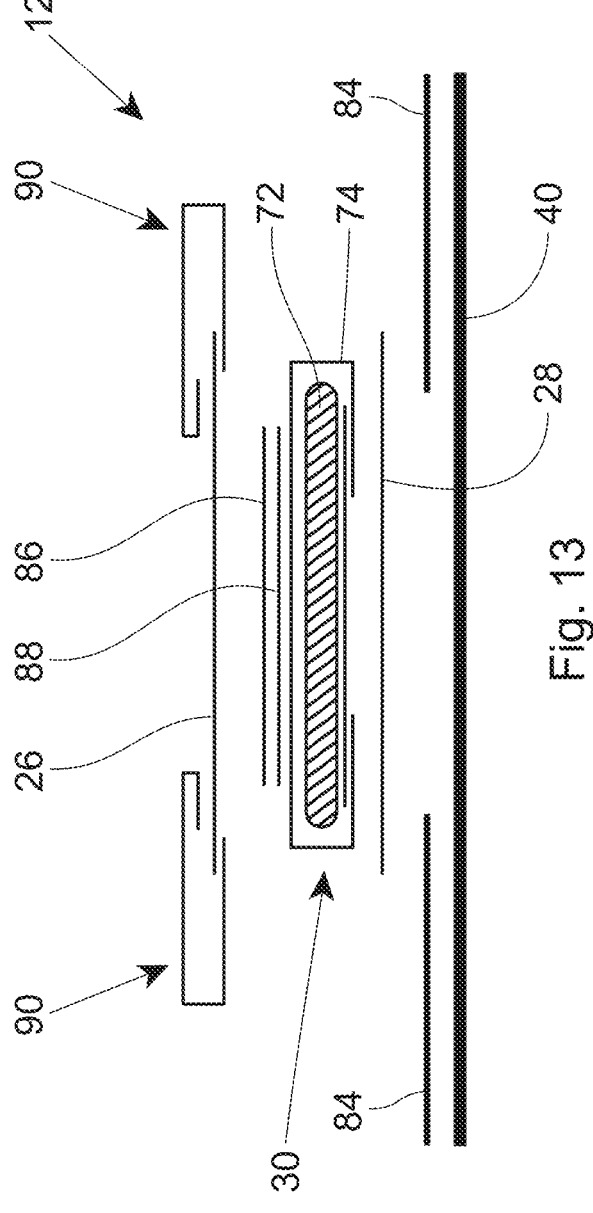
FIG. 13 is an example cross-sectional view taken within a front waist region of an absorbent article.
Figure 14:
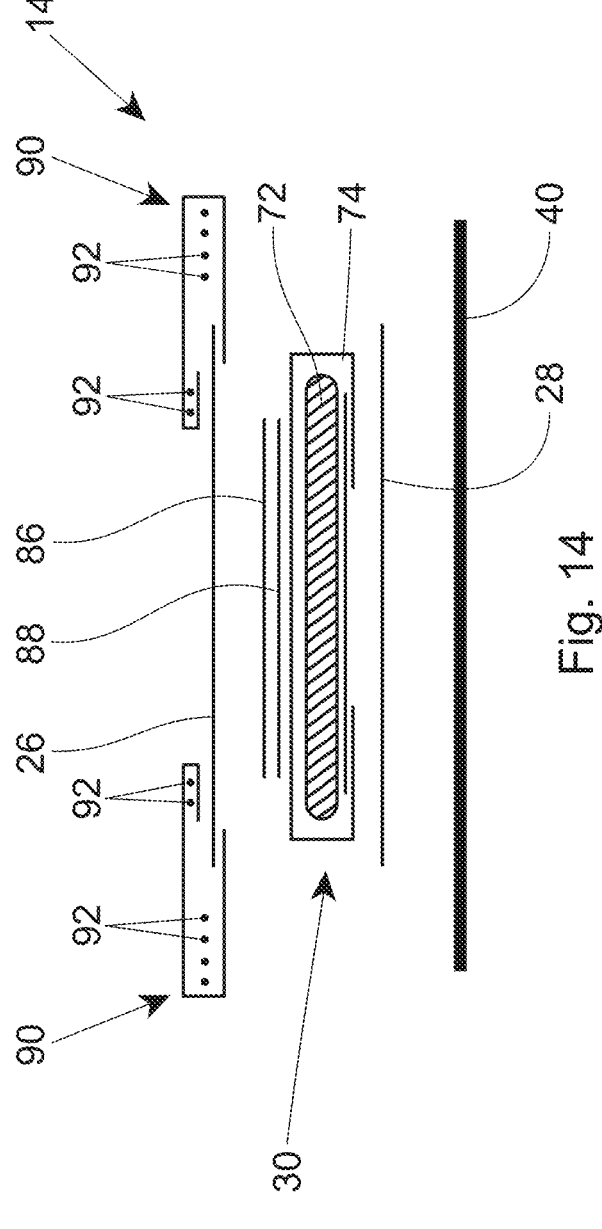
FIG. 14 is an example cross-sectional view taken within a crotch region of an absorbent article.
Figure 15:
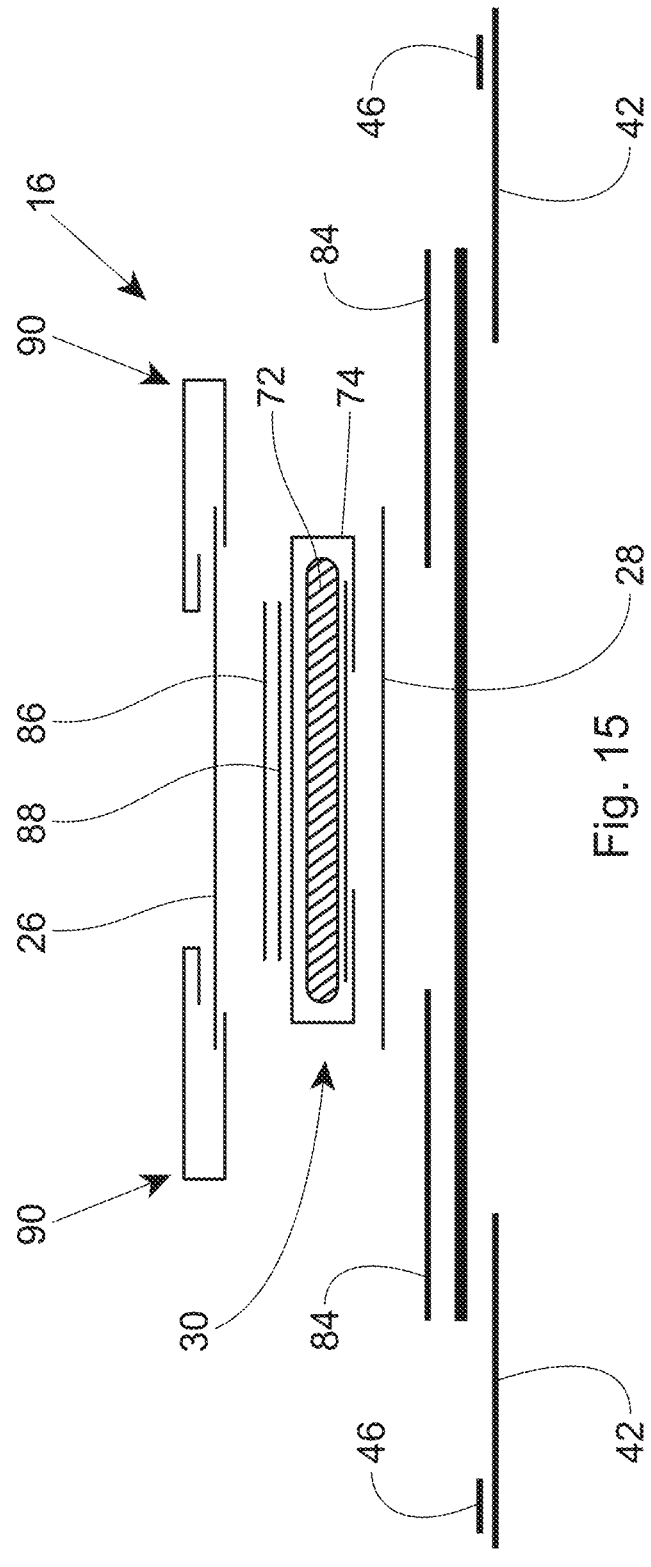
FIG. 15 is an example cross-sectional view taken within a back waist region of an absorbent article.

FIGS. 13-15 illustrate example cross-sectional views of absorbent articles within the scope of the present disclosure. FIG. 13 is an example cross-sectional view taken within a front waist region 12 of an absorbent article. FIG. 14 is an example cross-sectional view taken within a crotch region 14 of an absorbent article. FIG. 15 is an example cross-sectional view taken within a back waist region 16 of an absorbent article. In FIGS. 13-15, an outer cover material is element 40, a liquid permeable topsheet is element 26, opacity patches are elements 84, a liquid impermeable backsheet is element 28, an absorbent core is element 30, with the core bag being element 74, an absorbent material is element 72, and a distribution material is element 86. The distribution material 86 may comprise cross-linked cellulosic material and may be optional. An acquisition material is element 88. A liquid permeable topsheet is element 26. Barrier leg cuffs are elements 90. Elastics in the barrier leg cuffs are elements 92. Back ears are elements 42. Fasteners on the back ears 42 are elements 46. Construction glues and/or bonds between the various layers and/or components have been removed for clarity. Other cross-sectional configurations known to those of skill in the art are also within the scope of the present disclosure.

Substrates and/or Laminates for Absorbent Articles

Substrates and/or laminates for absorbent articles or other consumer products are provided herein. The substrates may comprise a through-air bonded nonwoven material or a lightly bonded nonwoven material. The absorbent articles discussed herein may comprise the substrates as a topsheet, an acquisition material, a secondary topsheet, an outer cover nonwoven, and/or other components, for example. The absorbent articles discussed herein may comprise the laminates as a topsheet laminate, a topsheet/acquisition material laminate, a topsheet/secondary topsheet laminate, a topsheet and other material laminate, an outer cover nonwoven material laminate, and/or other components, for example. The laminates may comprise two or more nonwoven materials, with at least one of the nonwoven materials being through-air bonded and free of normal calendar or point bonds. The substrates and/or laminates may also be used as wipes, cleaning or dusting substrates, or in other consumer products that comprise nonwoven materials. In some instances, the substrates and/or laminates may comprise wet-laid nonwoven materials, air-laid nonwoven materials, meltblown nonwoven materials, nano-fiber nonwoven materials, spunbond nonwoven materials, carded nonwoven materials, spunlace nonwoven materials, or combinations of the same.

FIGS. 16-19 are schematic cross-sectional examples of portions of laminates of the present disclosure. FIGS. 16-19 also illustrate the substrates (i.e., single layer) of the present disclosure (essentially remove the materials without the increased permeability regions). It is to be understood that the substrates may be used/manufactured independently of the laminates by only providing a single layer substrate with increased permeability regions (see FIGS. 16A and 19A showing only the one nonwoven material from FIGS. 16 and 19, respectively). The substrates 201 of FIGS. 16A and 19A will be described further below.

The laminates 200 may comprise a first nonwoven material 202 and a second nonwoven material 204. Any of the laminates discussed herein may also comprise at least a third nonwoven material 206, although only illustrated in the laminate 200 of FIG. 17. The laminates 200 may comprise a plurality of three-dimensional elements 208. The three-dimensional elements 208 may extend upward (e.g., FIGS. 16 and 17, toward a wearer) or downward (e.g., FIGS. 18 and 19, away from a wearer). The three-dimensional elements 208 may be tufts, projections, and/or raised or depressed regions and may have any suitable shapes (such as ovate, circular, for example), heights, widths, and/or areas. The laminates 200 may comprise land areas 210 and increased permeability regions 212. The land areas 210 may be present in the laminates 200 in areas free of the three-dimensional elements 208 and free of the increased permeability regions 212. The land areas 210 are essentially portions of the laminates that are not subjected to the strains of three-dimensional element formation and remain generally planar and unchanged in basis weight. The laminates 200 may comprise the increased permeability regions 212 adjacent to the three-dimensional elements 208. These increased permeability regions 212 are illustrated in dash in FIGS. 16-19A. The increased permeability regions 212 are essentially areas of low basis weight (relative to the remainder of the nonwoven materials, such as the land areas 210) in the first or second nonwoven materials, although they could exist in both of or more than two of the nonwoven materials. In some instances, areas of low basis weight may only exist in a through-air bonded nonwoven material or a light bonded nonwoven material and not in a normal calendar bonded or point bonded nonwoven material.

Figures 16, 16A:
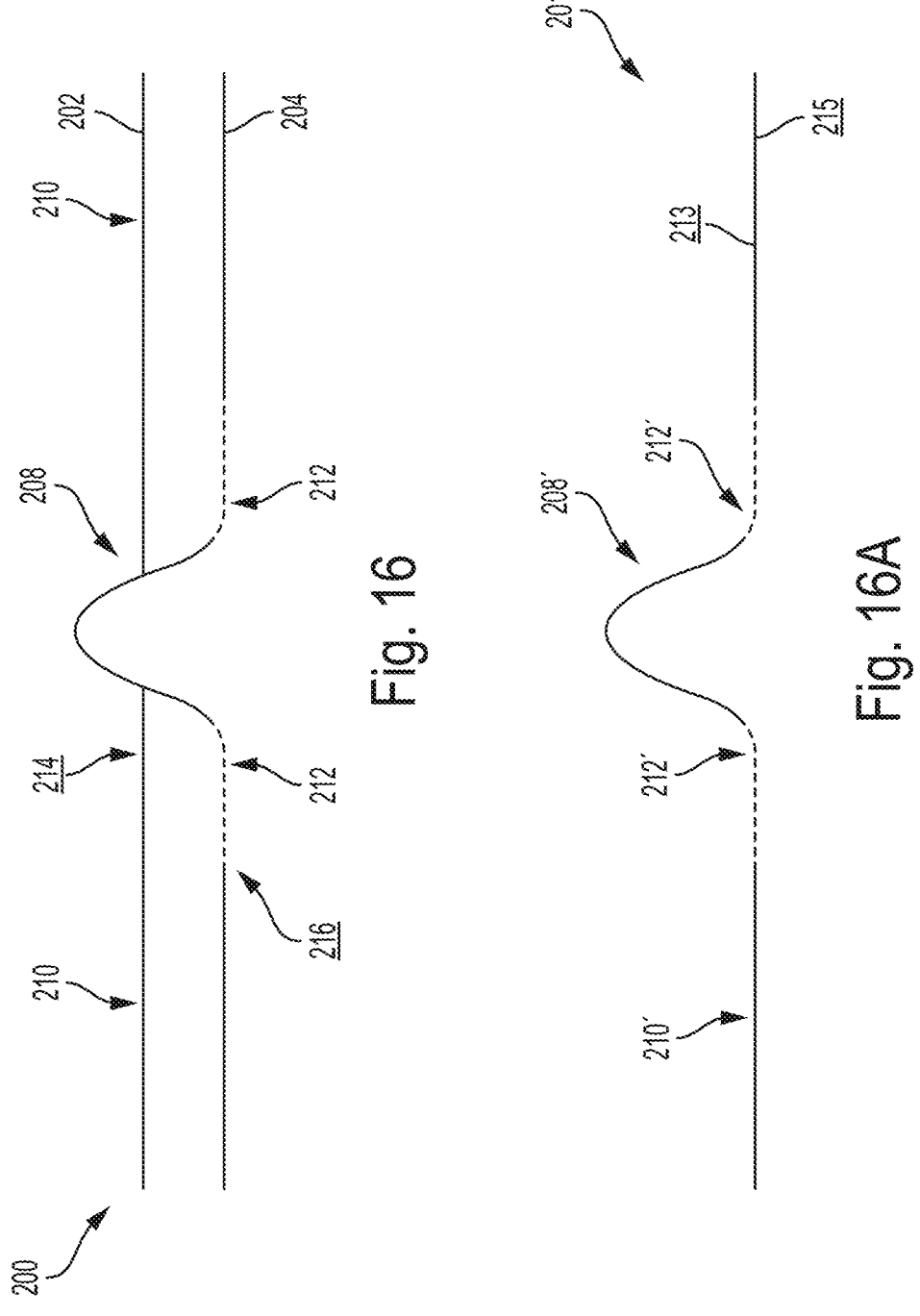
FIG. 16 is a cross-sectional schematic illustration of an example laminate of the present disclosure comprising two nonwoven materials.
FIG. 16A is a cross-sectional schematic illustration of an example substrate of the present disclosure comprising a nonwoven material.
Figures 17, 18:
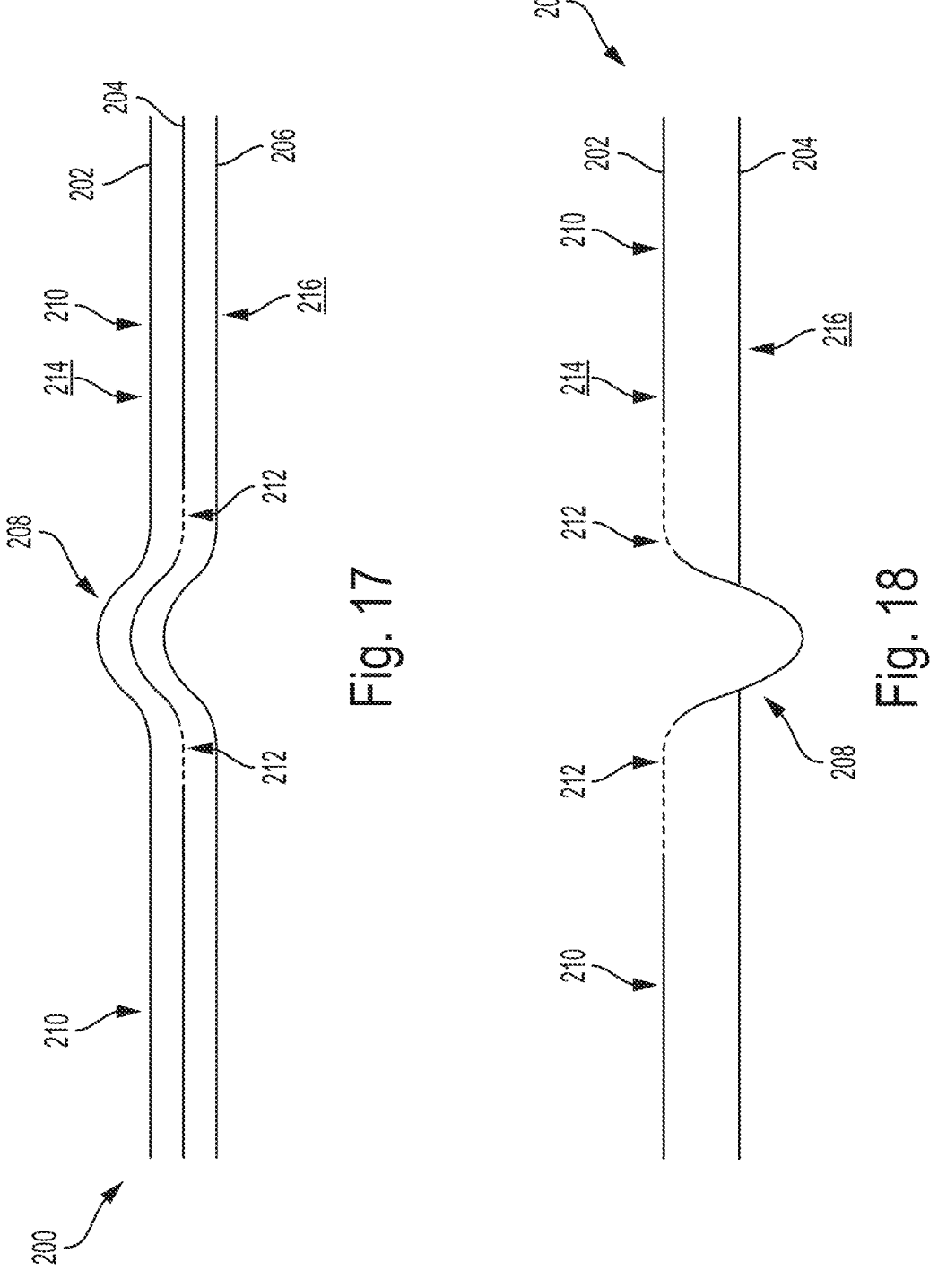
FIG. 17 is a cross-sectional schematic illustration of another example laminate of the present disclosure comprising three nonwoven materials.
FIG. 18 is a cross-sectional schematic illustration of another example laminate of the present disclosure comprising two nonwoven materials.

FIG. 16 illustrates a portion of the second nonwoven material 204 extending through the first nonwoven material 202 to form a three-dimensional element 208 in the laminate 200. The second nonwoven material 204 may also be a substrate of the present disclosure. A first surface 214 of the laminate 200 may comprise portions of the first nonwoven material 202 and portions of the second nonwoven material 204, while the second surface 216 may only comprise the second nonwoven material 204. In such an instance, the second nonwoven material 204 may comprise the increased permeability regions 212 adjacent to the three-dimensional elements 208. FIG. 18 illustrates a portion of the first nonwoven material 202 extending through the second nonwoven material 204. In such an instance, the second surface 216 of the laminate may comprise portions of the first nonwoven material 202 and portions of the second nonwoven material 204, while the first surface 214 may only comprise the first nonwoven material 202. In such an instance, the first nonwoven material 202 may comprise the increased permeability regions 212 adjacent to the three-dimensional elements 208.

Figures 19, 19A:
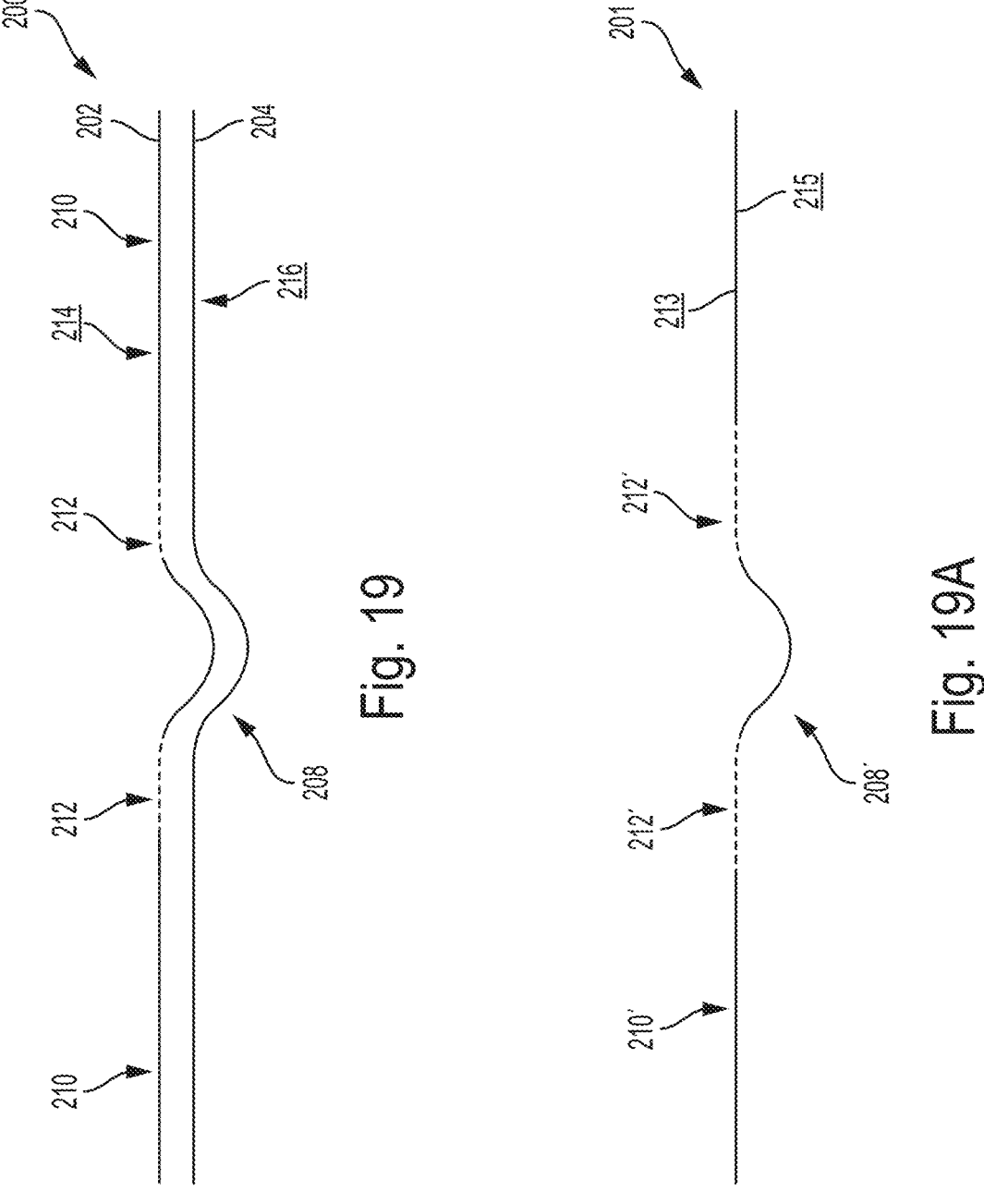
FIG. 19 is a cross-sectional schematic illustration of another example laminate of the present disclosure comprising two nonwoven materials.
FIG. 19A is a cross-sectional schematic illustration of an example substrate of the present disclosure comprising a nonwoven material.

FIG. 17 illustrates a portion of the second nonwoven material 204, and optionally a third nonwoven material or material 206 (such as a film or a nonwoven), nested with the first nonwoven material 202 to form a three-dimensional element 208. In such an instance, the increased permeability regions 212 may be formed in at least the second nonwoven material 204 adjacent to the three-dimensional elements 208, and possibly in the first nonwoven material 202 in similar locations as the second nonwoven material 204. FIG. 19 illustrates a portion of the first nonwoven material 202 nested with the second nonwoven material 204 to form a three-dimensional element 208. In such an instance, the increased permeability regions 212 may be formed in at least the first nonwoven material 202 adjacent to the three-dimensional elements 208, and possibly in the second nonwoven material 204 in similar locations as the first nonwoven material 202.

FIG. 16A illustrates an example substrate 201 taken from FIG. 16. The substrate 201 is the second nonwoven material 204 of FIG. 16. The substrate 201 has a first surface 213 and second surface 215. The substrate 201 comprises three-dimensional elements 208', land areas 210', and increased permeability regions 212'. The increased permeability regions 212' may be positioned adjacent to at least some of the three-dimensional elements 208'. In the land areas 210', the nonwoven material has a first basis weight, according to the Micro-CT Test. In the increased permeability regions 212', the nonwoven material has a second basis weight in the range of less than 75% to less than 25% of the first basis weight of the land areas. The three-dimensional elements 208' of the example substrate 201 of FIG. 16A may extend upwardly (as illustrated) or downwardly. Other details discussed herein may apply to the substrate 201, such a material choices, fiber types, bonds etc.

FIG. 19A illustrates an example substrate 201 taken from FIG. 19. The substrate 201 is the first nonwoven material 202 of FIG. 19. The substrate 201 has a first surface 213 and second surface 215. The substrate 201 comprises three-dimensional elements 208', land areas 210', and increased permeability regions 212'. The increased permeability regions 212' may be positioned adjacent to at least some of the three-dimensional elements 208'. In the land areas 210', the nonwoven material has a first basis weight, according to the Micro-CT Test. In the increased permeability regions 212', the nonwoven material has a second basis weight in the range of less than 75% to less than 25% of the first basis weight of the land areas. The three-dimensional elements 208' of the example substrate 201 of FIG. 19A may extend downwardly (as illustrated) or upwardly. Other details discussed herein may apply to the substrate 201, such as material choices, fiber types, bonds etc.

Figure 20:
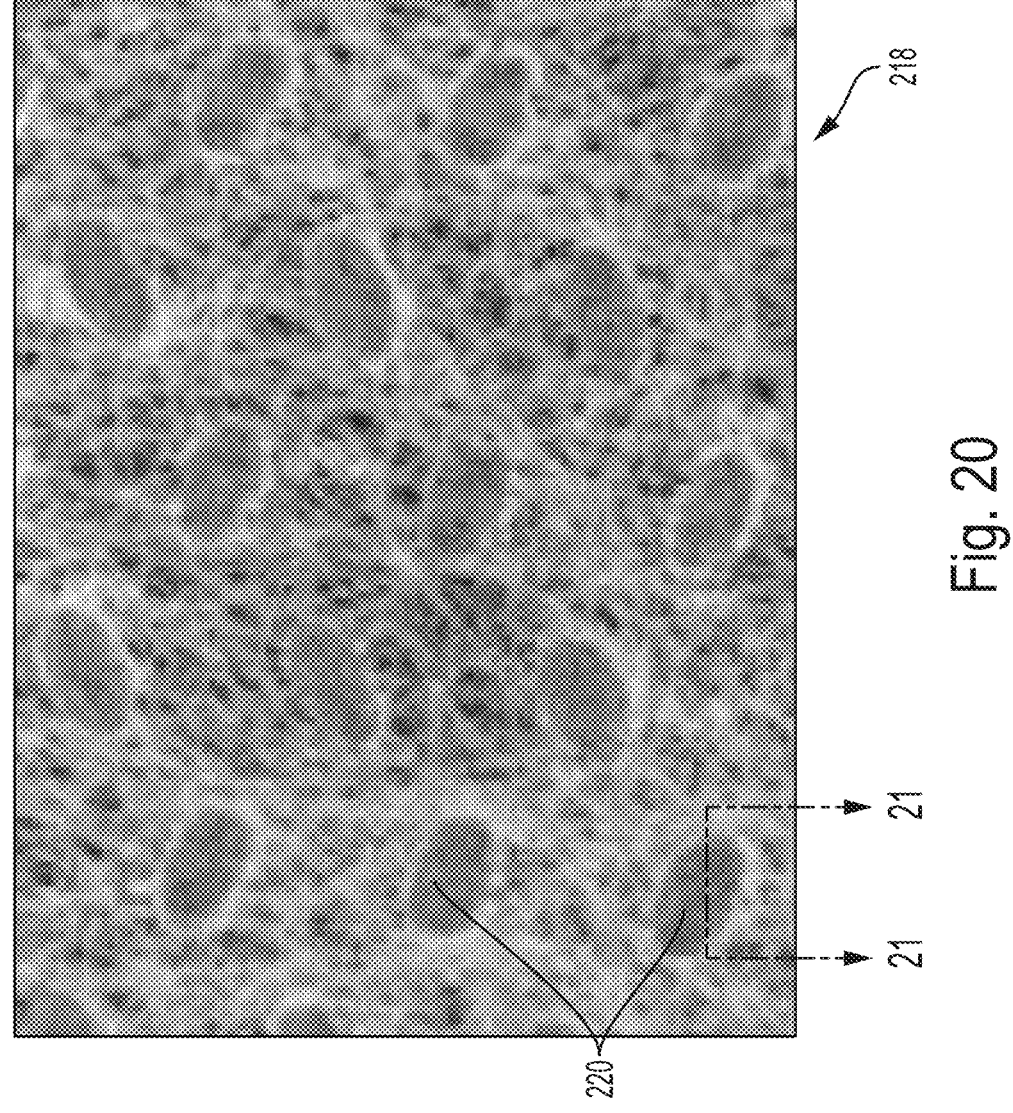
FIG. 20 is a top view photograph of a calendar or point bonded nonwoven material for use in the laminates of the present disclosure.
Figure 21:
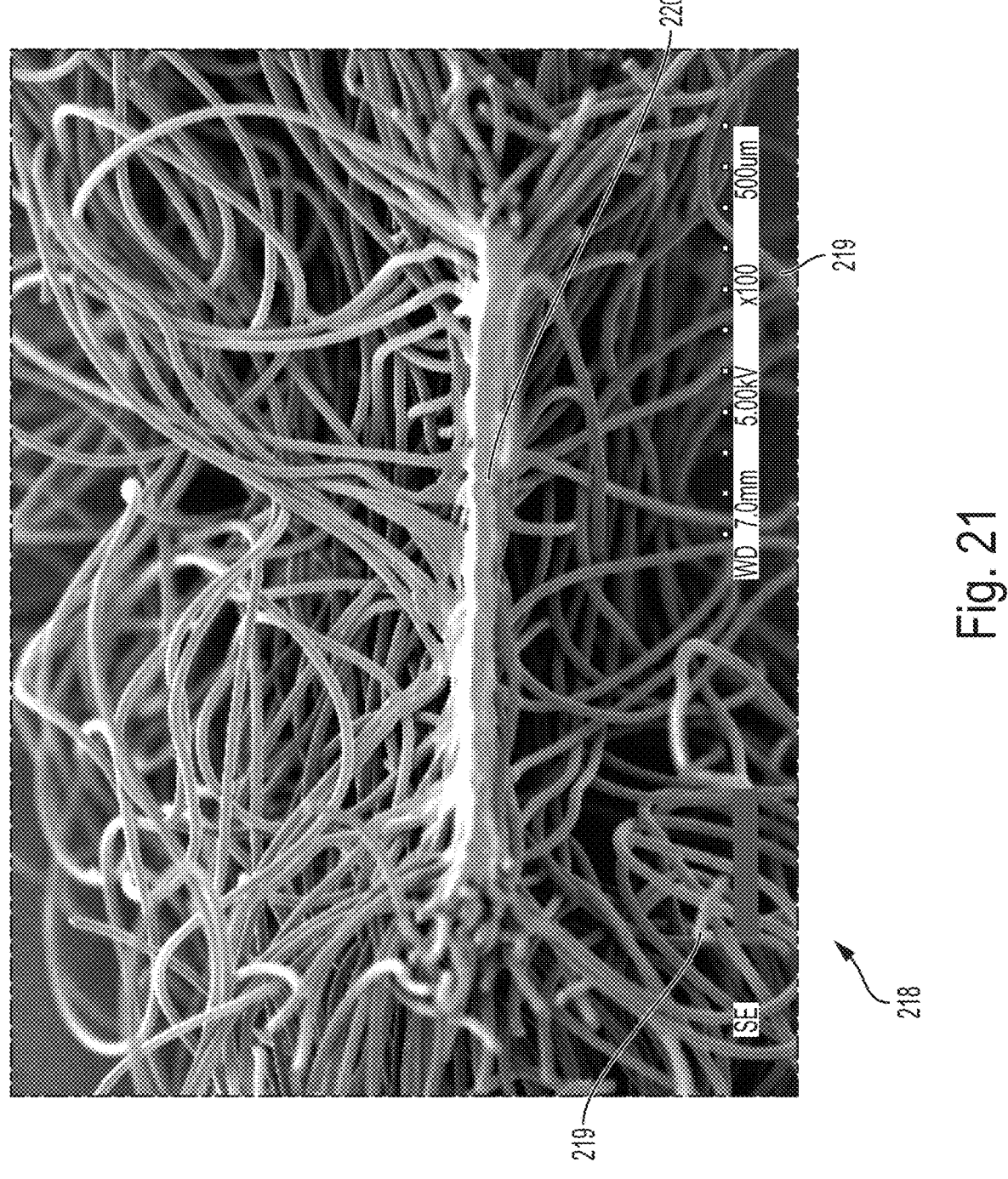
FIG. 21 is a cross-sectional photograph taken about line 21-21 of FIG. 20 and illustrating the calendar or point bond.

FIG. 20 illustrates a top view photograph of a calendar or point bonded nonwoven material 218 that may be used in the laminates described herein as one or more of the nonwoven materials. FIG. 21 is a cross-sectional schematic illustration taken about line 21-21 of FIG. 20. FIG. 21 illustrates a calendar or point bond 220 surrounded by unbonded fibers 219. The calendar or point bonds 220 are essentially highly densified regions within the nonwoven material 218 and are sometimes referred to herein as "normal calendar or point bonds." These normal calendar or point bonds typically have uniform sizes, shapes, and are uniformly spaced relative to each other. The normal calendar or point bonds 220 may be used during the nonwoven material manufacturing process to join some of the fibers 219 of a fibrous web together to form the nonwoven materials and provide them with integrity. Typically, these normal calendar or point bonds are created by conveying the fibrous web through a nip between a calendar roll having plurality of nubs (that create the bonds) and an anvil roll, as is generally known in the art. The normal calendar or point bonded nonwoven materials for the laminates of the present disclosure may comprise continuous fiber nonwoven materials (e.g., spunbond nonwoven materials) or may comprise carded fiber nonwoven materials. The calendar or point bonded nonwoven materials may also comprise other types of fibers such as natural fibers (e.g., cotton) or a blend of natural and synthetic fibers.

Figure 22:
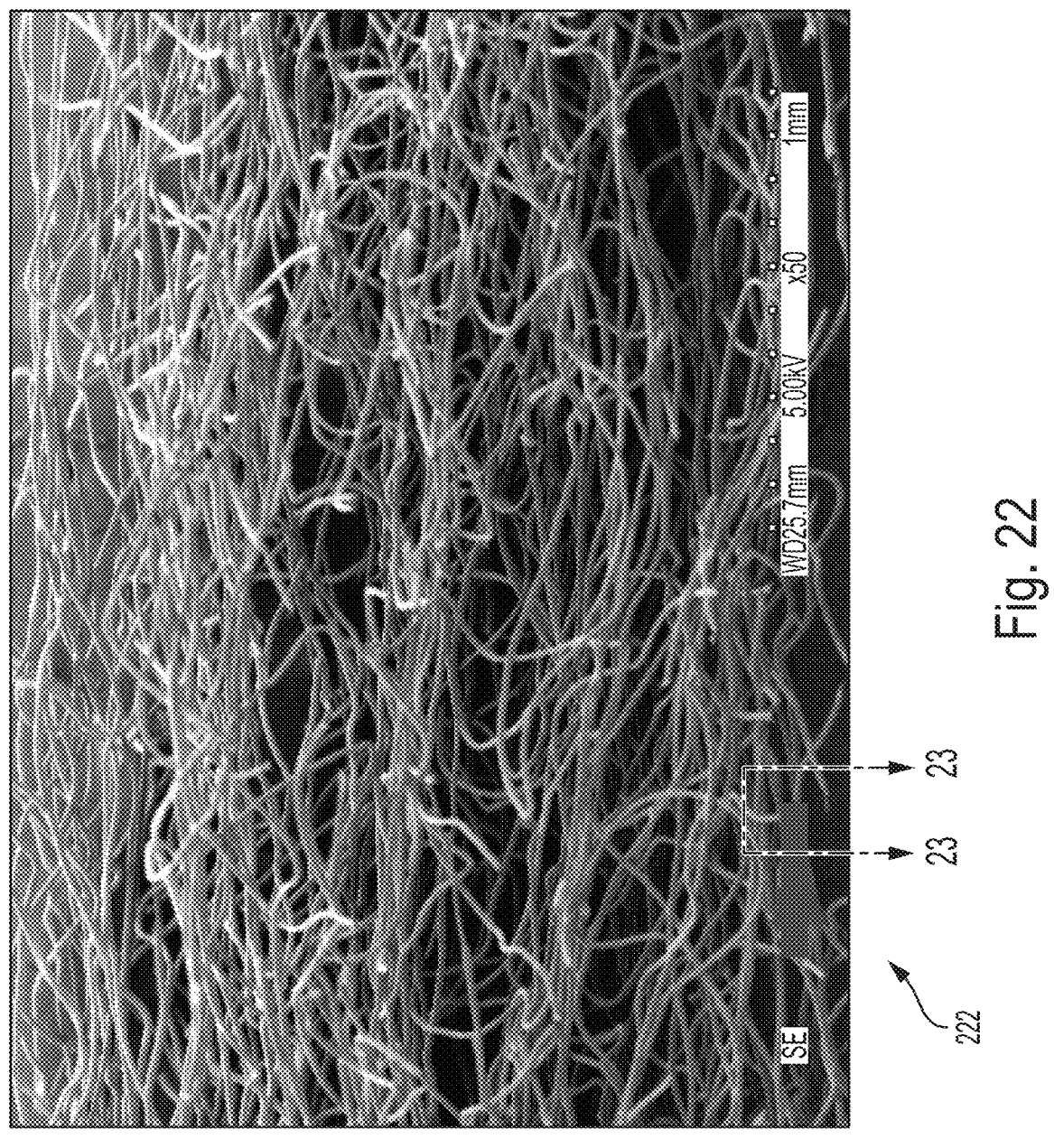
FIG. 22 is a side view photograph of a through-air bonded nonwoven material for use in the laminates of the present disclosure.
Figure 23:
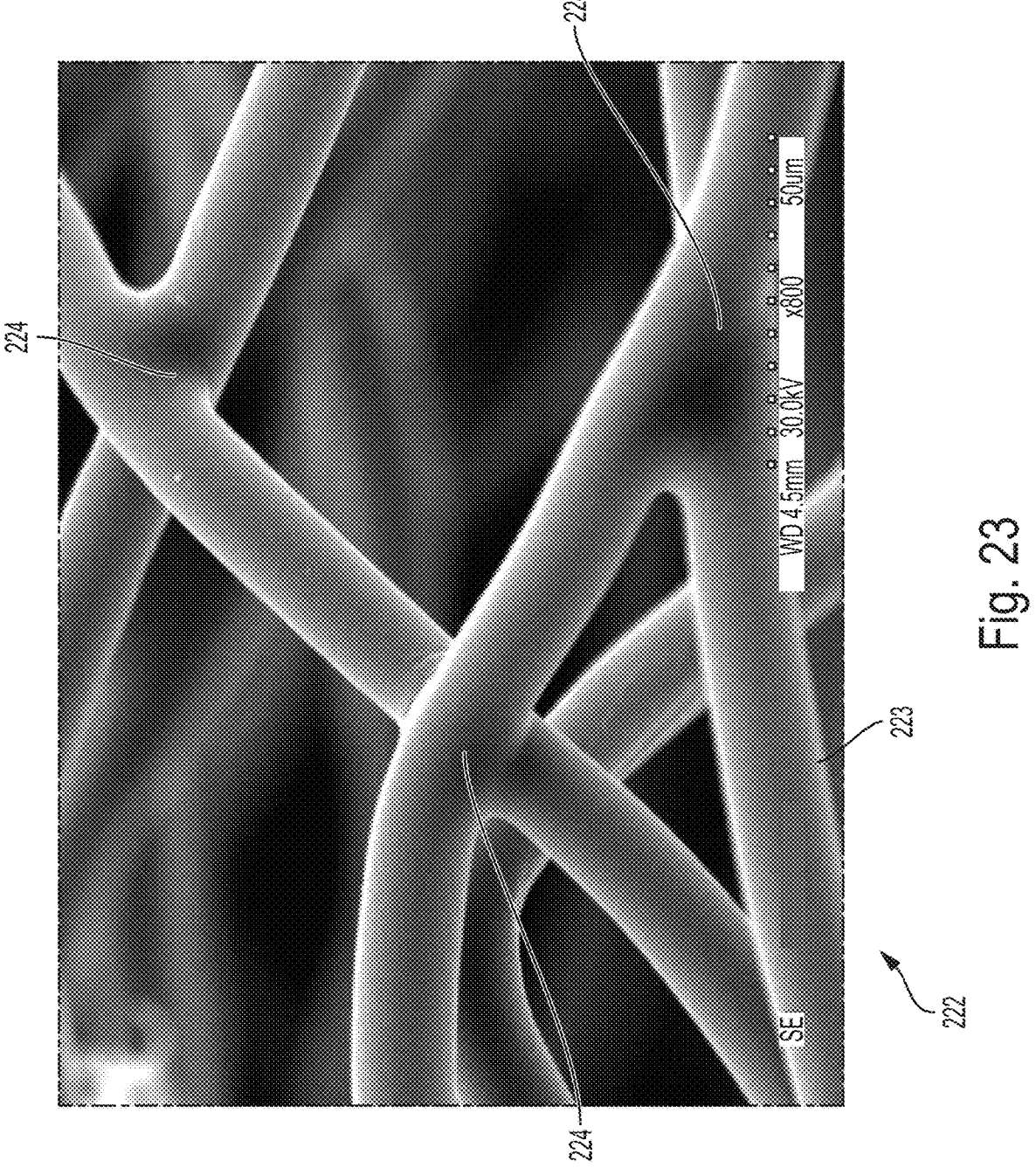
FIG. 23 is a cross-sectional photograph taken about line 23-23 of FIG. 22 and illustrating through-air bonds.

In contrast to normal calendar or point bonds, fibers of a fibrous web may be through-air bonded to form a nonwoven material. Through-air bonding processes create many more and smaller bonds in a nonwoven material compared to normal calendar or point bonds. Typically through-air bonds are created by passing heated or hot air through a fibrous web. Through-air bonds are formed where fibers 223 of the fibrous web contact each other, typically by melting of the fiber intersections. Individual through-air bonds are much weaker than normal calendar or point bonds as these bonds are each formed only between a few fibers (e.g., 2 fibers to 5 fibers). FIG. 22 is a side view photograph of a through-air bonded nonwoven material 222 comprising a plurality of through-air bonds 224. FIG. 23 is a cross-sectional photograph taken about line 23-23 of FIG. 22. As can be seen in FIG. 23, the through-air bonds 224 occur at, at least some of the fiber intersections and are quite plentiful. The through-air bonded nonwoven materials may only comprise fiber to fiber bonds and may not comprise any other bonds. Though-air bonded nonwoven materials for the laminates of the present disclosure may comprise continuous fiber nonwoven materials (e.g., spunbond materials) or may comprise carded fiber nonwoven materials. The through-air bonded nonwoven materials may also comprise other types of fibers such as natural fibers (e.g., cotton, pulp, bamboo) or a blend of natural and synthetic fibers.

Also, in contrast to normal calendar or point bonds, fibers of a fibrous web may be lightly calendar or point bonded to form a nonwoven material. In such an instance, nubs of a bonding roll may apply less pressure to the fibrous web than normal calendar or point bonds (i.e., FIG. 21). By applying less pressure to the fibrous web, the fibrous web is less densified than normal calendar or point bonds and forms lightly bonded calendar or point bonds. Fibers within the lighted bonded calendar or point bonds are able to break free from or move within the bonds more than fibers within the normal calendar or point bonds during three-dimensional element formation. Typically, fibers within normal calendar or point bonds break during three-dimensional element formation causing loose fiber ends and reducing softness. By having lightly bonded calendar or point bonds, fiber breakage may be reduced and improved softness may be achieved.

Owing to the nature of through-air bonds and/or lightly bonded calendar or point bonds, these nonwoven materials may allow for more fiber movement when creating three-dimensional elements therein. Stated another way, through-air bonds and/or lightly bonded calendar or point bonds in a nonwoven material may allow basis weight of the nonwoven materials to be shifted proximate to or adjacent to the three-dimensional elements. This fiber movement and/or basis weight shifting is believed to be due to through-air bonds between individual fibers breaking upon application of an applied strain (i.e., three-dimensional element formation). The same fiber movement may be noticed in nonwoven materials that comprise lightly bonded calendar or point bonds. The same phenomenon has not been seen in normal calendar or point bonded nonwoven materials owing to the strength of the calendar or point bonds. As such, the substrates and/or laminates of the present disclosure may employ at least one through-air bonded nonwoven material or at least one nonwoven material comprising lightly bonded calendar or point bonds. The second or additional materials of a laminate may be through-air bonded nonwoven materials, nonwoven materials comprising lightly bonded calendar or point bonds, or may be normal calendar or point bonded nonwoven materials. The through-air bonded nonwoven materials may be bonded at low temperatures (i.e., gas passing through the nonwoven materials is of a low temperature), thereby creating low strength bonds between individual fibers. This may allow the fibers to essentially pull out of the bonds and allow for improved fiber mobility compared to normal calendar or point bonds.

Referring again to FIG. 16, the second nonwoven material 204 may be a through-air bonded nonwoven material or a nonwoven material comprising lightly bonded calendar or point bonds. As such, when the three-dimensional elements 208 are formed in the laminate 200, fibers of the second nonwoven material 204 may move into the three-dimensional elements 208 and leave a low basis weight, increased permeability region 212 adjacent to or proximate to the three-dimensional elements 208. As stated above, this fiber movement out of the increased permeability regions 212 into the three-dimensional elements 208 is believed to be made possible by the use of the through-air bonded nonwoven materials or nonwoven materials comprising lightly bonded calendar or point bonds. The first nonwoven material 202 may be a normal calendar or point bonded nonwoven material, may be a through-air bonded nonwoven material, or may be a nonwoven material comprising lightly bonded calendar or point bonds. When referring to an increased permeability region herein, it will be understood that even if the low basis weight area is only in one of the nonwoven materials, the overall laminate will still have an increased permeability in that area.

Referring to FIG. 17, the first and/or third nonwoven materials may comprise through-air bonded nonwoven materials, normal calendar or point bonded nonwoven materials, or nonwoven materials comprising lighted bonded calendar or point bonds. If the first and/or third nonwoven materials comprise through-air bonded nonwoven materials or nonwoven materials comprising lighted bonded calendar or point bonds, increased permeability regions may be created in the first and third nonwoven materials in areas overlapping the increased permeability regions 212 in FIG. 17. The same may apply to the second nonwoven material of FIG. 19.

The first nonwoven material 202 of FIG. 18 may be a through-air bonded nonwoven material or nonwoven material comprising lightly bonded calendar or point bonds. The second nonwoven material 204 of FIG. 18 may be a through-air bonded nonwoven material, a nonwoven material comprising lightly bonded calendar or point bonds, or a normal calendar or point bonded material.

The increased permeability regions allow for faster bodily exudate acquisition, especially in combination with the three-dimensional elements. Consumers desire bodily exudates to be quickly removed from a wearer-facing surface of an absorbent article and quickly absorbed by the absorbent articles. The increased permeability regions may even help bodily exudate acquisition when the first nonwoven material 202 is more hydrophobic than the second nonwoven material 204. A hydrophobic wearer-facing layer (e.g., first nonwoven material 202) may be desirable to minimize rewet and maintain a clean/dry surface for the wearer, however bodily exudate acquisition speeds may typically be slower. Often apertures are added to nonwoven materials to address this. Sometimes, however, texture is desired over apertures for softness, for the perception or reality of bodily exudates being able to come back up through the apertures, and/or for having texture to wipe the body, but still larger gushes of bodily exudates are required to be absorbed.

Referring generally to FIGS. 16-19, the first nonwoven material 202 may be hydrophobic, while the second nonwoven material 204 may be hydrophilic. In another instance, the first nonwoven material 202 may be more hydrophobic, or more hydrophilic, than the second nonwoven material 204. Likewise, the first nonwoven material 202 may have a different contact angle than the second nonwoven material 204. In other instances, both of the first nonwoven material 202 and the second nonwoven material 204 may be hydrophilic to the same degree or to different degrees. Referring specifically to FIG. 17, the third nonwoven material 206 may be more hydrophilic than the first and second nonwoven materials 202, 204. Referring to FIGS. 16A and 19A, the substrates 201 may be hydrophobic or hydrophilic as desired for an intended use.

Referring to FIGS. 16 and 18 generally, the land areas 210 of the laminate 200 may have a first basis weight and the increased permeability regions 212 of the laminate 200 may have a second basis weight. The first basis weight may be greater than the second basis weight. The three-dimensional elements 208 of the laminate 200 may have a third basis weight. The third basis weight may be less than the first basis weight, but greater than the second basis weight. Basis weight in this paragraph refers to total basis weight of all of the layers (except in the three-dimensional elements of FIGS. 16 and 18 since only one layer is present).

With respect to the laminate 200 of FIGS. 16 and 18, the second basis weight may be less than 50% to less than 5%, less than 45% to less than 5%, less than 40% to less than 5%, less than 35% to less than 5%, less than 30% to less than 5%, less than 25% to less than 5%, less than 20% to less than 5%, less than 15% to less than 5%, less than 50% to less than 10%, less than 45% to less than 10%, less than 40% to less than 10%, less than 35% to less than 10%, less than 30% to less than 10%, less than 25% to less than 10%, less than 20% to less than 10%, less than 15% to less than 10%, of the first basis weight, specifically reciting all 0.1% increments within the specified ranges and all ranges formed therein or thereby. All basis weight percentages discussed herein are according to the Micro-CT Test herein.

Referring to FIGS. 17 and 19 generally, the land areas 210 of the laminate 200 may have a first basis weight and the increased permeability regions 212 of the laminate 200 may have a second basis weight. The first basis weight may be greater than the second basis weight. The three-dimensional elements 208 of the laminate 200 may have a third basis weight. The third basis weight may be the same or substantially the same as the first basis weight and may be greater than the second basis weight. Basis weight in this paragraph refers to total basis weight of all of the layers.

With respect to the laminate 200 of FIGS. 17 and 19, the second basis weight may be less than 50% to less than 5%, less than 45% to less than 5%, less than 40% to less than 5%, less than 35% to less than 5%, less than 30% to less than 5%, less than 25% to less than 5%, less than 20% to less than 5%, less than 15% to less than 5%, less than 50% to less than 10%, less than 45% to less than 10%, less than 40% to less than 10%, less than 35% to less than 10%, less than 30% to less than 10%, less than 25% to less than 10%, less than 20% to less than 10%, less than 15% to less than 10%, of the first and/or third basis weights, specifically reciting all 0.1% increments within the specified ranges and all ranges formed therein or thereby. All basis weight percentages discussed herein are according to the Micro-CT Test herein.

Referring to FIGS. 16-19A generally, the land areas 210 or 210' of the nonwoven material having the increased permeability regions (212 or 212') may have a first basis weight and the increased permeability regions 212 of the nonwoven material 204 may have a second basis weight. The first basis weight may be greater than the second basis weight. The three-dimensional elements 208 of the second nonwoven materials 204 may have a third basis weight. The third basis weight may be the same or substantially the same as the first basis weight and may be greater than the second basis weight.

With respect to the nonwoven material discussed in the preceding paragraph, the second basis weight may be less than 50% to less than 5%, less than 45% to less than 5%, less than 40% to less than 5%, less than 35% to less than 5%, less than 30% to less than 5%, less than 25% to less than 5%, less than 20% to less than 5%, less than 15% to less than 5%, less than 50% to less than 10%, less than 45% to less than 10%, less than 40% to less than 10%, less than 35% to less than 10%, less than 30% to less than 10%, less than 25% to less than 10%, less than 20% to less than 10%, less than 15% to less than 10%, of the first and/or third basis weights, specifically reciting all 0.1% increments within the specified ranges and all ranges formed therein or thereby. All basis weight percentages discussed herein are according to the Micro-CT Test herein.

The fibers of the nonwoven material disclosed herein may comprise resins comprising polyolefins, PP, PE, copolymers, polyesters, bio-sourced materials, natural materials, or blends of the same.

The fibers of the nonwoven materials disclosed herein may comprise bicomponent fibers, such as PP/PE, PET/PE, PET/coPET, or PLA/PE, for example. The bicomponent fibers may have a core/sheath configuration, a concentric or eccentric core/sheath configuration, an islands-in-the-sea configuration, and/or any other suitable bicomponent configurations where at least a portion of a surface of the fibers comprises a lower melting component, for example.

As used herein, the term "non-round fiber(s)" describes fibers having a non-round cross-section, and includes "shaped fibers" and "capillary channel fibers." Such fibers may be solid or hollow, and they may be tri-lobal, delta-shaped, and may be fibers having capillary channels on their outer surfaces. The capillary channels may be of various cross-sectional shapes such as "U-shaped", "H-shaped", "C-shaped" and "V-shaped". The fibers may be round, hollow, or shaped, such as tri-lobal, ribbon, capillary channel fibers (e.g., 4DG). The fibers may comprise microfibers or nanofibers. The fibers may also have round cross-sectional shapes.

The basis weight of the overall substrates or laminates of the present disclosure may vary according to the intended purpose of the substrates or laminates. The basis weight of an overall laminate or substrate may be in the range of about 10 gsm (grams per square meter) to about 120 gsm, about 10 gsm to about 100 gsm, about 10 gsm to about 100 gsm, about 15 gsm to about 75 gsm, about 15 gsm to about 65 gsm, about 15 gsm to about 50 gsm, about 20 gsm to about 40 gsm, specifically reciting all 0.1 gsm increments within the specified ranges and all ranges formed therein or thereby.

The various nonwoven materials of the laminates discussed herein may have the same color or different colors. In some instances, a first nonwoven material may be a first, non-white color, and a second nonwoven material may be white or may be a second non-white color. As an example, the first nonwoven material may be white and the second nonwoven material may be teal, or vice versa. As another example, the first nonwoven material may be teal and the second nonwoven material may be blue, or vice versa. The substrates discussed herein may be a non-white color as well.

The various nonwoven materials of a laminate may have different opacities. For instance, a first nonwoven material of a laminate may have a different opacity as a second nonwoven material of the laminate. The first and second nonwoven materials may have an opacity difference in the range of about 10% to about 70%, about 15% to about 60%, about 15% to about 50%, about 20% to about 50%, specifically reciting all 0.1% increments within the specified ranges and all ranges formed therein or thereby.

Figure 24:
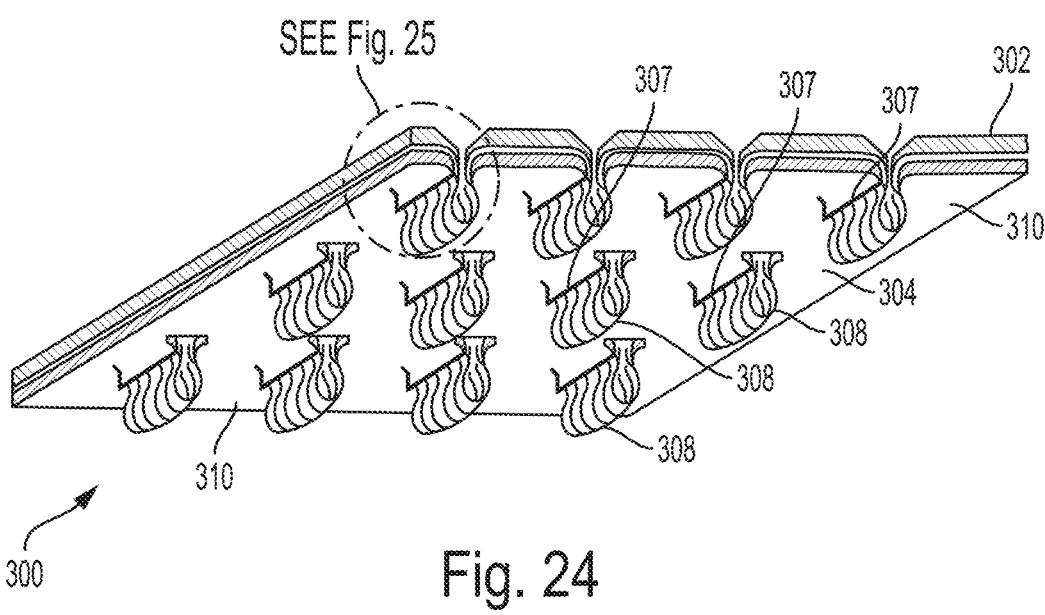
FIG. 24 is a bottom perspective view of another example laminate of the present disclosure.
Figure 25:
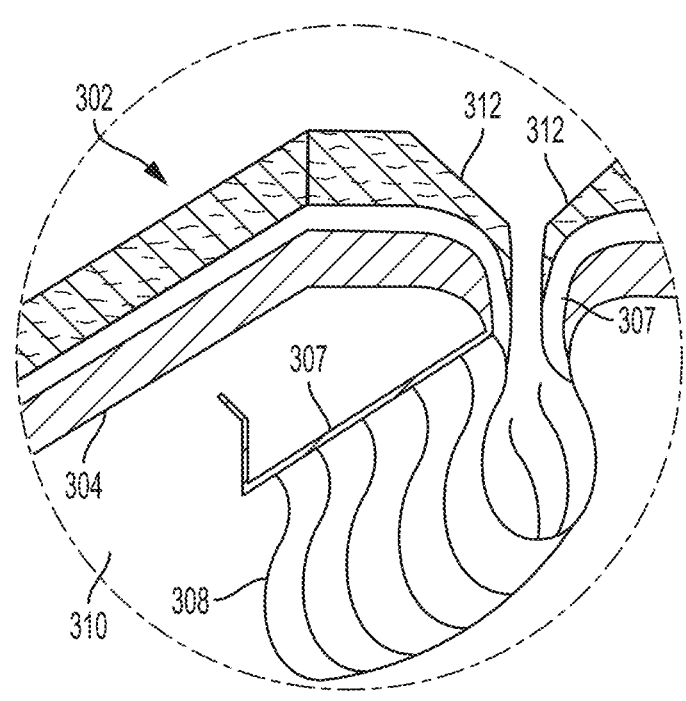
FIG. 25 is an exploded view of circle 25 of FIG. 24.

FIGS. 24 and 25 illustrate another laminate 300 of the present disclosure, wherein portions of the first nonwoven material 302 extend through openings 307 in the second nonwoven material 304 to form three-dimensional elements 308 in the laminate 300. It is to be recognized that the second nonwoven material 304 may instead extend through openings in the first nonwoven material 302 depending on whether it is desired to have the three-dimensional elements 308 facing upwardly or downwardly. FIG. 24 is a bottom perspective view of the laminate 300. FIG. 25 is an exploded view of the circle 25 of FIG. 24. The laminate 300 may also comprise land areas 310 and increased permeability regions 312 (similar to that described above with respect to increased permeability regions 212). Low basis weight areas of the increased permeability regions 312 may occur in the first nonwoven material 302 in the example of FIGS. 24 and 25. As such, the first nonwoven material 302 may be a through-air bonded material, such as a carded through-air bonded material, for example. The first nonwoven material 302 may also be a nonwoven material comprising lightly bonded calendar or point bonds. The second nonwoven material 304 may be a through-air bonded material or a calendar or point bonded material. Additional materials may also be provided in the laminate.

Suitable example processes for producing the laminates and substrates of the present disclosure are detailed in U.S. Pat. No. 7,553,532 to Turner et al (see e.g., FIGS. 7-10 and associated disclosure).

In view of the fiber movement allowed by the use of the first nonwoven material 302 that is a through-air bonded nonwoven material or nonwoven material comprising lightly bonded calendar or point bonds, fibers of the three-dimensional elements may have substantially constant fiber diameters. Fibers in three-dimensional elements without the use of a through-air bonded nonwoven material or nonwoven material comprising lightly bonded calendar or point bonds, typically have thinned or broken fibers in three-dimensional elements owing to the lack of fiber movement allowed, such as in normal calendar or point bonded nonwoven materials. By allowing for fiber movement (e.g., using through-air bonded nonwoven materials), there are many more types of fibers possible, since the fibers do not need to be extensible to stretch or thin during the three-dimensional element formation. For example, PE/PET fibers are not typically extensible and may break upon applied strain if the fibers are not able to pull out of the bond sites. A further advantage of using a through-air bonded material or a nonwoven material comprising lightly bonded calendar or point bonds as the first nonwoven material may be fuller tufts with unbroken fibers, or less broken fibers in the tufts compared to a normal calendar or point bonded nonwoven material.

Sum of Bond Strength vs. Sum of Fiber Breakage Strength

The substrates and/or laminates comprising a nonwoven material comprising the increased permeability regions may comprise bonds joining the fibers. The nonwoven material may be a through-air bonded nonwoven material or a nonwoven material comprising lightly bonded calendar or point bonds. The bonds may each have a bond strength. The fibers may each have a fiber yield or breakage strength. A sum of the bond strengths in an area of the nonwoven material may be less than a sum of the fiber yield or breakage strengths in the area of the nonwoven material. Individual bonds strengths may be less than individual fiber yield or breakage strengths to allow individual bonds to come apart and enable individual fibers to move vs. stretch (i.e., yield) or break. The area may at least partially or fully coincide with the increased permeability regions. By having the sum of the bonds strengths being less than the sum of the fiber breakage strengths, it is believed that the bonds in the area typically break before the fibers in the area, thereby leading to improved fiber movement when three-dimensional elements are created, and, thereby reducing fiber breakage during three-dimensional element creation.

Films

A laminate may comprise a film in combination with a through-air bonded nonwoven material or nonwoven material comprising lightly bonded calendar or point bonds. The film may be the first layer and the through-air bonded nonwoven material or nonwoven material comprising lightly bonded calendar or point bonds may be the second layer. The laminate may comprise land areas and three-dimensional elements in both layers and increased permeability regions in the through-air bonded nonwoven material or nonwoven material comprising lightly bonded calendar or point bonds.

Test Methods

All samples are conditioned in an environment maintained at 23±2° C. and 50±2% relative humidity for 24 hours prior to testing.

Fiber Diameter and Denier Test

The diameter of fiber in a sample of a nonwoven material is determined by using a Scanning Electron Microscope (SEM) and image analysis software. A magnification of 500 to 10,000 times is chosen such that the filaments are suitably enlarged for measurement (such that at least 3-5 pixels cross the diameter ("width") of a fiber). The samples are sputtered with gold or a palladium-gold compound to avoid electric charging and vibrations of the fibers in the electron beam. A manual procedure for determining the fibers diameters is used. Using a mouse and a cursor tool, the edge of a randomly selected fiber is sought and then measured across its width (i.e., perpendicular to fiber direction at that point) to the other edge of the fiber. For non-circular fibers, the area of the cross-section is measured using the image analysis software by analyzing the Z-plane cross-sections of the fibers. The effective diameter is then calculated by calculating the diameter as if the found area was that of a circle. A scaled and calibrated image analysis tool provides the scaling to get actual reading in micrometers ($\mu$m). Several fibers in the three-dimensional elements of the nonwoven material are thus randomly selected across the sample of the nonwoven material using the SEM. At least two specimens from the nonwoven material in the three-dimensional elements are cut and tested in this manner. Altogether, at least 100 such measurements are made and then all data are recorded for statistical analysis. The recorded data are used to calculate average (mean) of the fiber diameters, standard deviation of the fiber diameters, and median of the fiber diameters. Another useful statistic is the calculation of the amount of the population of fiber that is below a certain upper limit. To determine this statistic, the software is programmed to count how many results of the fiber diameters are below an upper limit and that count (divided by total number of data and multiplied by 100%) is reported in percent as percent below the upper limit, such as percent below 1 micrometer diameter or %-submicron, for example.

If the results are to be reported in denier, then the following calculations are made.

Fiber Diameter in denier=Cross-sectional area (in m2)*density (in kg/m3)*9000 m*1000 g/kg.

For round fibers, the cross-sectional area is defined by the equation:

$$A=\pi*(D/2)^2.$$

The density for polypropylene, for example, may be taken as 910 kg/m3.

Given the fiber diameter in denier, the physical circular fiber diameter in meters (or micrometers) is calculated from these relationships and vice versa. We denote the measured diameter (in microns) of an individual circular fiber as D.

In case the fiber have non-circular cross-sections, the measurement of the fiber diameter is determined as and set equal to the hydraulic diameter, as discussed above.

The fiber cross sectional shape may be determined from the above images of the cross-sections in the Z-plane as well. The nonwoven fibers near the first surface of the nonwoven material should be evaluated for cross-sectional shape. The cross-sectional shape of the fibers near the first surface of the nonwoven material should be recorded. Nonwoven fibers near the second surface of the nonwoven material should be evaluated for cross-sectional shape. The cross-sectional shape of the fibers near the second surface of the nonwoven material should be recorded.

Micro-CT Test

The micro-CT measurement method calculates basis weight values within different regions of a laminate or substrate sample, such as three-dimensional elements, lands areas, and increased permeability regions formed adjacent to the three-dimensional elements and positioned intermediate at least some of the land areas and at least some of the three-dimensional elements. Basis weight is based on analysis of a 3D x-ray sample image obtained on a micro-CT instrument (a suitable instrument is the Scanco μCT 50 available from Scanco Medical AG, Switzerland, or equivalent). The micro-CT instrument is a cone beam microtomograph with a shielded cabinet. A maintenance free x-ray tube is used as the source with an adjustable diameter focal spot. The x-ray beam passes through the sample, where some of the x-rays are attenuated by the sample. The extent of attenuation correlates to the mass of material the x-rays have to pass through. The transmitted x-rays continue on to the digital detector array and generate a 2D projection image of the sample. A 3D image of the sample is generated by collecting several individual projection images of the sample as it is rotated, which are then reconstructed into a single 3D image. The instrument is interfaced with a computer running software to control the image acquisition and save the raw data. The 3D image is then analyzed using image analysis software (suitable image analysis software are MATLAB available from The Mathworks, Inc., Natick, MA, and Avizo Lite available from Visualization Sciences Group/FEI Company, Burlington, MA, or equivalents) to measure the basis weight of regions within the laminate or substrate sample.

Sample Preparation

To obtain a sample for measurement, lay a single layer of the dry sample out flat and die cut/punch out a circular piece with a diameter of approximately 20 mm. If the sample is in the form of a laminate, die cut/punch out a circular sample with a diameter of approximately 20 mm that includes all layers of the laminate. The laminate sample may be analyzed either as the intact multi-layer structure, or separated into individual substrate layers for analysis, so long as separation of the laminate layers does not physically deform or alter the structure of the individual layer.

If the substrate/laminate is a layer of an absorbent article, for example a topsheet, backsheet nonwoven, acquisition layer, distribution layer, or other component layer; tape the absorbent article to a rigid flat surface in a planar configuration. Carefully separate the individual substrate/laminate from the absorbent article. A scalpel and/or cryogenic spray (such as Cyto-Freeze, Control Company, Houston TX) can be used to remove a substrate/laminate from additional underlying layers, if necessary, to avoid any longitudinal and lateral extension of the substrate/laminate. Once the substrate/laminate has been removed from the absorbent article, proceed with die cutting/punching out the sample as described above.

If the substrate/laminate is in the form of a wet wipe, open a new package of wet wipes and remove the entire stack from the package. Remove a single wipe from the middle of the stack, lay it out flat and allow it to dry completely prior to die cutting/punching out the sample for analysis.

A sample may be cut from any location containing the regions to be analyzed. Care should be taken to avoid folds, wrinkles or tears when selecting a location for sampling.

Image Acquisition

Set up and calibrate the micro-CT instrument according to the manufacturer's specifications. Place the sample into the appropriate holder, between two rings of low density material. This will allow the central portion of the sample to lay horizontal and be scanned without having any other materials directly adjacent to its upper and lower surfaces. Measurements should be taken in this region. The 3D image field of view is approximately 15 mm on each side in the XY-plane with a resolution of approximately 3400 by 3400 pixels, and with a sufficient number of 4.5 micron thick slices collected to fully include the z-direction of the sample. The reconstructed 3D image resolution contains isotropic voxels of 4.5 microns. Images are acquired with the source at 45 kVp and 88-200 μA with no additional low energy filter. These current and voltage settings may be optimized to produce the maximum contrast in the projection data with sufficient x-ray penetration through the sample, but once optimized held constant for all substantially similar samples. A total of 1500 projections images are obtained with an integration time of 500 ms and 4 averages. The projection images are reconstructed into the 3D image, and saved in 16-bit RAW format to preserve the full detector output signal for analysis.

Image Processing

The 3D dataset is loaded into the image analysis software, and trimmed (cropped) to a rectangular prism 3D image of the analysis region by removing the surrounding holder and the low density mounting material from the 3D dataset. Trimming is performed such that the maximum amount of the sample in the analysis region is retained in the 3D image, and the empty space above and below the sample is minimized. The trimmed 3D image is scaled from 16-bit to 8-bit, and thresholded using Otsu's method, which calculates the threshold level that minimizes the weighted intra-class variance, to separate and remove the background signal due to air, but maintain the signal from the fibers within the sample image.

The thresholded 3D image is oriented so that the upper surface is as close to parallel with the XY-plane as possible.

A Basis Weight image is generated from the thresholded 3D image. To generate this image, the value for each voxel in an XY-plane slice is summed with all of its corresponding voxel values in the other z-direction slices containing signal from the sample. This creates a 2D image where each pixel now has a value equal to the cumulative signal through the entire sample.

In order to convert the raw data values in the Basis Weight Image into real values, a basis weight calibration curve is generated. Obtain a substrate/laminate that is of substantially similar composition to the sample being analyzed and has a uniform basis weight. Follow the procedures described above to obtain at least ten replicate samples of the calibration curve substrate. Accurately measure the basis weight, by taking the mass to the nearest 0.0001 g and dividing by the sample area and converting to grams per square meter (gsm), of each of the single layer calibration samples and calculate the average to the nearest 0.01 gsm. Following the procedures described above, acquire a micro-CT image of a single layer of the calibration sample substrate. Following the procedure described above, process the micro-CT image, and generate a Basis Weight Image containing raw data values. The real basis weight value for this sample is the average basis weight value measured on the calibration samples. Next, stack two layers of the calibration samples on top of each other, and acquire a micro-CT image of the two layers of calibration material. Generate a basis weight raw data image of both layers together, whose real basis weight value is equal to twice the average basis weight value measured on the calibration samples. Repeat this procedure of stacking single layers of the calibration substrate, acquiring a micro-CT image of all of the layers, generating a raw data basis weight image of all of the layers, the real basis weight value of which is equal to the number of layers times the average basis weight value measured on the calibration samples. A total of at least four different basis weight calibration images are obtained. The basis weight values of the calibration samples must include values above and below the basis weight values of the original sample being analyzed to ensure an accurate calibration. The calibration curve is generated by performing a linear regression on the raw data versus the real basis weight values for the four calibration samples. This linear regression must have an $R^2$ value of at least 0.95, if not repeat the entire calibration procedure. This calibration curve is now used to convert the raw data values into real basis weights.

Micro-CT Basis Weight

Begin by identifying the region to be analyzed. A region to be analyzed may be a three-dimensional element, a lands area, or an increased permeability region formed adjacent to a three-dimensional element and positioned intermediate at least some of the land areas and at least some of three-dimensional elements. Next, identify the boundary of the region to be analyzed. Once the boundary of the region has been identified, draw an oval or circular "region of interest" (ROI) within the interior of the region. The ROI should have an area of at least 0.1 mm², and be selected to measure an area with basis weight values representative of the identified region. Calculate the average basis weight within the ROI. Record this value as the region's basis weight to the nearest 0.01 gsm.

Example

In this example, a two layer nonwoven laminate of the present disclosure was compared to a two layer comparative example laminate. A single layer substrate of the present disclosure was also compared to a single layer comparative example substrate. Measurements were taking according to the Micro-CT Test herein. Measurements were taken on the two layer laminate (laminates herein) and on only the bottom layer (substrates herein) of the example nonwoven material and the comparative example nonwoven material.

The example nonwoven material of the present disclosure had a first (top) layer and a second (bottom) layer. The top layer was a normal calendar bonded, 25 gsm nonwoven material of polyethylene/polypropylene sheath/core bicomponent spunbond fibers. The bottom layer was a through-air bonded, 25 gsm nonwoven material of carded hydrophilic polyethylene fibers. The layers were tufted together (see e.g., FIG. 24) using a 0.060 pitch tooling at a depth of engagement of 0.115 inches and a line speed of 1,000 feet per minute. Example suitable tooling is illustrated in FIGS. 7-10 of U.S. Pat. No. 7,553,532 to Turner et al.

The comparative example material had a first (top) layer and a second (bottom) layer. The top layer was a normal calendar bonded, 25 gsm nonwoven material of polyethylene/polypropylene sheath/core bicomponent spunbond fibers. The bottom layer was a normal calendar bonded, hydrophilic 25 gsm nonwoven material of polyethylene/polypropylene sheath/core bicomponent spunbond fibers.

The top layers were the same in both the example nonwoven material and in the comparative example nonwoven material.

Figure 26:
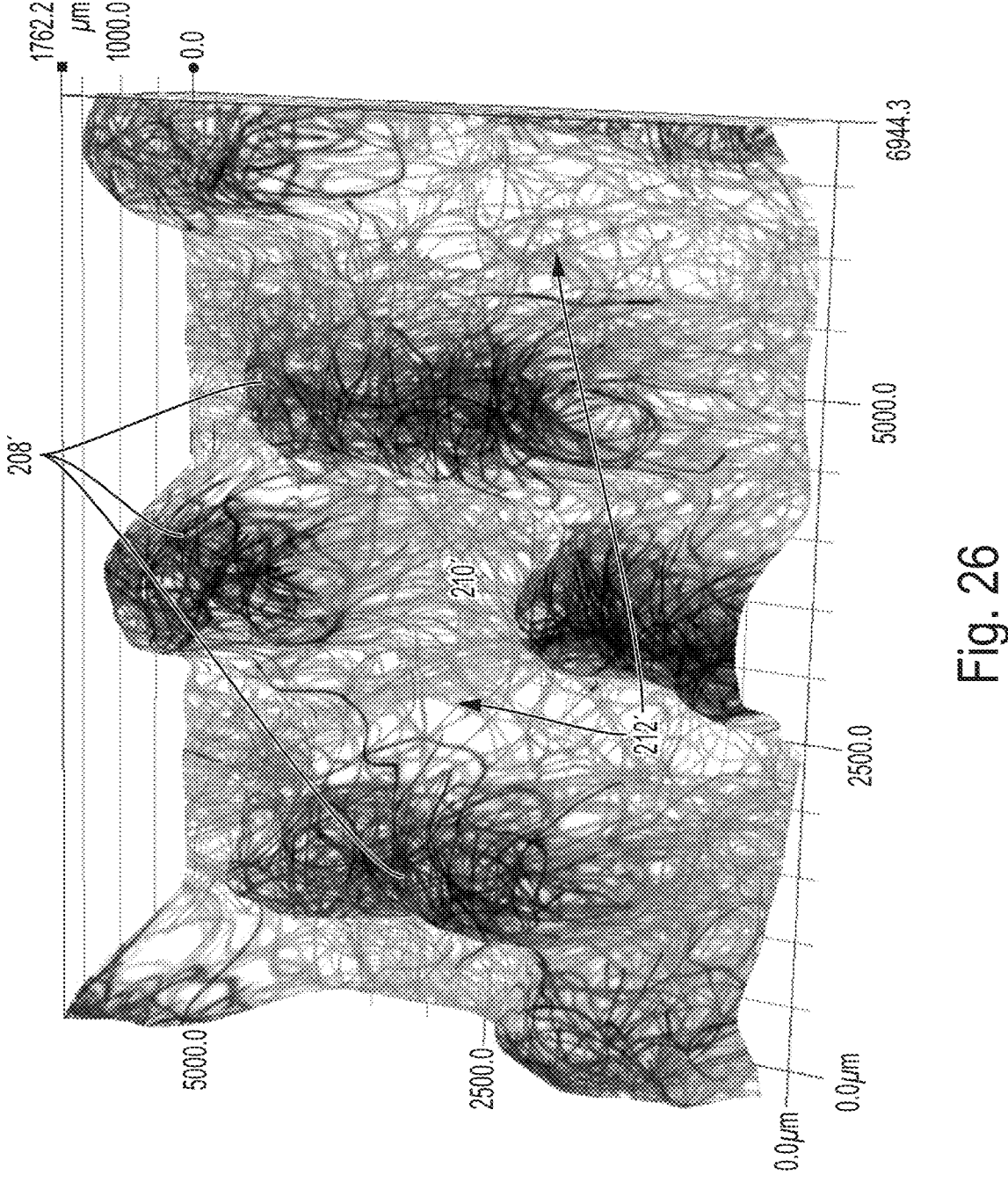
FIG. 26 is a top perspective view photograph of an example substrate of the present disclosure comprising a nonwoven material having increased permeability regions.
Figure 27:
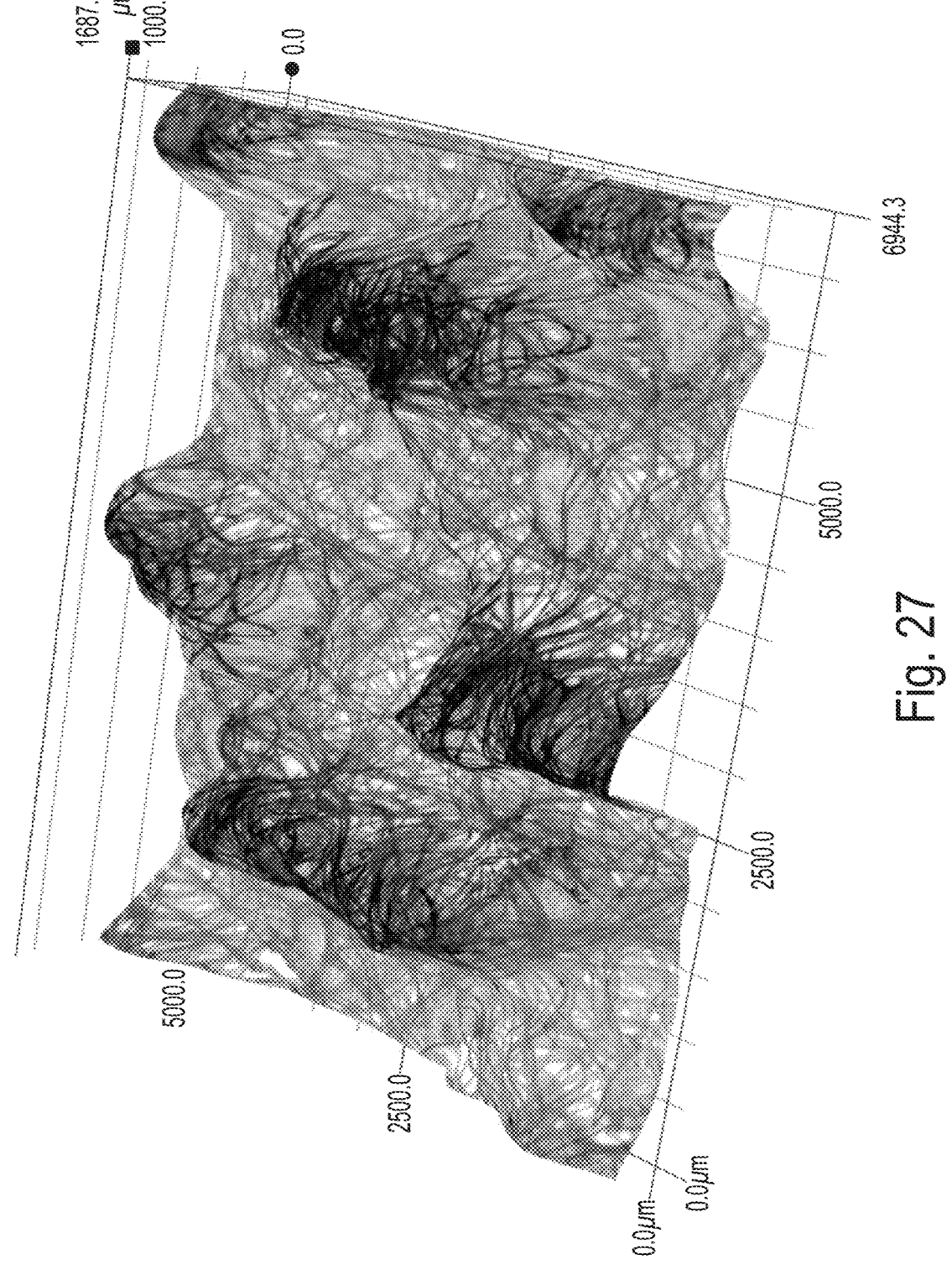
FIG. 27 is a top perspective view photograph of a comparative example substrate that does not comprise the increased permeability regions of the present disclosure. The comparative example substrate is a 25 gsm spunbond PE/PP bicomponent nonwoven material comprising calendar bonds.

The example of the present disclosure nonwoven material comprising increased permeability regions is illustrated in FIG. 26. The comparative example material that does not comprise increased permeability regions and that does comprise calendar bonds is illustrated in FIG. 27.

| | Land Area Basis Weight (gsm) | Increased Permeability Region Basis Weight (gsm) | Basis Weight Change |
|---|---|---|---|
| Two Layer (Laminate) | | | |
| Present Disclosure Example Bico/Carded HL | 50.2 | 36.7 | 23% |
| Comparative Example Bico/Bico | 47.4 | 42.8 | 9.6% |
| Lower Layer Only (Substrate) | | | |
| Present Disclosure Example Bico/Carded HL | 24.6 | 12.7 | 48% |
| Comparative Example Bico/Bico-Prior Art | 21.7 | 17.1 | 21% |

Combinations

Paragraph 1. A liquid permeable laminate for an absorbent article, the laminate comprising:

a first nonwoven material;

a second nonwoven material, wherein the second nonwoven material comprises through-air bonds;

portions of the second nonwoven material extending into or through the first nonwoven material to form three-dimensional elements in the laminate;

land areas in the laminate in areas free of the three-dimensional elements;

wherein, in the land areas, the laminate has a first basis weight, according to the Micro-CT Test;

increased permeability regions formed in the laminate adjacent to three-dimensional elements and intermediate at least some of the land areas and at least some of the three-dimensional elements;

wherein the increased permeability regions have a second basis weight in the range of less than 50% to less than 5% of the first basis weight of the land areas, according to the Micro-CT Test.

Paragraph 2. The laminate for an absorbent article of Paragraph 1, wherein the first nonwoven material has a third basis weight in the land areas, wherein the first nonwoven material has a fourth basis weight in the increased permeability regions, and wherein the third basis weight is substantially the same as the fourth basis weight.

Paragraph 3. The laminate for an absorbent article of Paragraph 2, wherein the second nonwoven material has a fifth basis weight in the land areas, wherein the second nonwoven material has a sixth basis weight in the increased permeability regions, and wherein the sixth basis weight is in the range of less than 75% to less than 25% of the fifth basis weight, according to the Micro-CT Test.

Paragraph 4. The laminate for an absorbent article of any one of the preceding Paragraphs, wherein the second nonwoven material is free of calendar or point bonds and comprises only fiber to fiber bonds.

Paragraph 5. The laminate for an absorbent article of any one of the preceding Paragraphs, wherein the portions of the second nonwoven material extend through the first nonwoven material to form the three-dimensional elements in the laminate, and wherein a first surface of the laminate comprises portions of the first nonwoven material and portions of the second nonwoven material.

Paragraph 6. The laminate for an absorbent article of any one of the preceding Paragraphs, wherein the first nonwoven material comprises calendar bonds.

Paragraph 7. The laminate for an absorbent article of any one of Paragraphs 1-5, wherein the first nonwoven material comprises through-air bonds, and wherein the first nonwoven material is free of calendar or point bonds and comprises only fiber to fiber bonds.

Paragraph 8. The laminate for an absorbent article of any one of the preceding Paragraphs, wherein the first nonwoven material comprises continuous fibers.

Paragraph 9. The laminate for an absorbent article of any one of the preceding Paragraphs, wherein the first nonwoven material has a different contact angle than the second nonwoven material.

Paragraph 10. The laminate for an absorbent article of any one of the preceding Paragraphs, wherein the second nonwoven material comprises carded fibers.

Paragraph 11. The laminate for an absorbent article of any one of Paragraphs 1-9, wherein the second nonwoven material comprises continuous fibers.

Paragraph 12. The laminate for an absorbent article of any one of the preceding Paragraphs, wherein fibers of the second nonwoven material have a substantially constant fiber diameter in the three-dimensional elements.

Paragraph 13. The laminate for an absorbent article of any one of the preceding Paragraphs, wherein the first nonwoven material and/or the second nonwoven material comprises bicomponent fibers.

Paragraph 14. The laminate for an absorbent article of any one of the preceding Paragraphs, wherein the second basis weight of the increased permeability regions is in the range of less than 30% to less than 5% of the first basis weight of the land areas, according to the Micro-CT Test.

Paragraph 15. The laminate for an absorbent article of any one of the preceding Paragraphs, wherein the first nonwoven material has a first opacity, wherein the second nonwoven material has a second opacity, and wherein the first opacity is different than the second opacity.

Paragraph 16. The laminate for an absorbent article of any one of the preceding Paragraphs, wherein the first nonwoven material has a first color, wherein the second nonwoven material has a second color, and wherein the first color is different than the second color.

Paragraph 17. An absorbent article comprising:
the laminate of any one of the preceding Paragraphs;
a liquid impermeable backsheet;
an absorbent core disposed at least partially intermediate the laminate and the liquid impermeable backsheet.

Paragraph 18. The absorbent article of Paragraph 17, wherein the laminate forms the topsheet in the absorbent article.

Paragraph 19. The absorbent article of Paragraph 17, wherein the laminate forms the topsheet and the acquisition layer or secondary topsheet in the absorbent article.

Paragraph 20. The absorbent article of any one of Paragraphs 17-19, wherein the absorbent article is a diaper or pant, and wherein the diaper or the pant comprises leg cuffs.

Paragraph 21. The absorbent article of any one of Paragraphs 17-19, wherein the absorbent article is a sanitary napkin.

Paragraph 22. A liquid permeable laminate for an absorbent article, the laminate comprising:
a first material;
a second nonwoven material, wherein the second nonwoven material comprises through-air bonds;
portions of the second nonwoven material extending into or through the first material to form three-dimensional elements in the laminate;
land areas in the laminate in areas free of the three-dimensional elements;
wherein, in the land areas, the laminate has a first basis weight, according to the Micro-CT Test;
increased permeability regions formed in the laminate adjacent to three-dimensional elements and intermediate at least some of the land areas and at least some of the three-dimensional elements;
wherein the increased permeability regions have a second basis weight in the range of less than 50% to less than 5% of the first basis weight of the land areas, according to the Micro-CT Test.

Paragraph 23. The laminate for an absorbent article of Paragraph 22, wherein the first material is a film.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited herein, including any cross referenced or related patent, patent publication, or patent application, is hereby incorporated by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular forms of the present disclosure have been illustrated and described, those of skill in the art will recognize that various other changes and modifications can be made without departing from the spirit and scope of the invention. It is therefore intended to cover in the appended claims all such changes and modifications that are within the scope of the present disclosure.

What is claimed is:
1. An absorbent article comprising:
a front waist region;
a back waist region;
a crotch region positioned intermediate the front waist region and the back waist region;
a substrate;
a liquid impermeable backsheet;
an absorbent core disposed at least partially intermediate the substrate and the liquid impermeable backsheet; and
a pair of back ears extending from the back waist region;
wherein the substrate comprises a nonwoven material comprising:
fibers;

three-dimensional elements;

land areas comprising the fibers and positioned in areas free of the three-dimensional elements;

wherein, in the land areas, the nonwoven material has a first basis weight, according to the Micro-CT Test;

increased permeability regions comprising the fibers and positioned adjacent to at least some of the three-dimensional elements and intermediate at least some of the three-dimensional elements and at least some of land areas; and wherein, in the increased permeability regions, the nonwoven material has a second basis weight in the range of 75% to 25% less than the first basis weight of the land areas, according to the Micro-CT Test.

2. The absorbent article of claim 1, wherein the nonwoven material comprises through-air bonds between at least some of the fibers.

3. The absorbent article of claim 1, wherein the nonwoven material comprises a through-air bonded material.

4. The absorbent article of claim 1, wherein the nonwoven material comprises bonds joining at least some of the fibers, the bonds each having a bond strength, the fibers each having a fiber breakage strength, wherein a sum of the bond strengths in an area of the nonwoven material is less than a sum of the fiber breakage strengths in the area of the nonwoven material.

5. The absorbent article of claim 4, wherein the area of the nonwoven material at least partially coincides with the increased permeability regions.

6. The absorbent article of claim 1, wherein, in the three-dimensional elements, the nonwoven material has a third basis weight, and wherein the third basis weight is substantially the same as the first basis weight of the land areas, according to the Micro-CT Test.

7. The absorbent article of claim 1, wherein the nonwoven material is hydrophobic.

8. The absorbent article of claim 1, wherein the nonwoven material is hydrophilic.

9. The absorbent article of claim 1, wherein the fibers comprise carded fibers.

10. The absorbent article of claim 1, wherein the fibers comprise continuous fibers.

11. The absorbent article of claim 1, wherein the increased permeability regions have a second basis weight in the range of 60% to 35% less than the first basis weight of the land areas, according to the Micro-CT Test.

12. The absorbent article of claim 1, wherein the fibers have a substantially constant fiber diameter in the three-dimensional elements, according to the Fiber Diameter and Denier Test.

13. The absorbent article of claim 1, wherein the fibers comprise bicomponent fibers.

14. An absorbent article comprising:

a front waist region;

a back waist region;

a crotch region positioned intermediate the front waist region and the back waist region;

a substrate;

a liquid impermeable backsheet;

an absorbent core disposed at least partially intermediate the substrate and the liquid impermeable backsheet; and a pair of back ears extending from the back waist region;

wherein the substrate comprises a nonwoven material comprising:

fibers;

through-air bonds between at least some of the fibers, wherein the nonwoven material is free of calendar or point bonds;

three-dimensional elements;

land areas comprising the fibers and positioned in areas free of the three-dimensional elements;

wherein, in the land areas, the nonwoven material has a first basis weight, according to the Micro-CT Test;

increased permeability regions comprising the fibers and positioned adjacent to at least some of the three-dimensional elements;

wherein the increased permeability regions have a second basis weight in the range of 75% to 25% less than the first basis weight of the land areas, according to the Micro-CT Test.

15. The absorbent article of claim 14, wherein the nonwoven material is hydrophobic.

16. The absorbent article of claim 14, wherein the nonwoven material is hydrophilic.

17. The absorbent article of claim 14, wherein the fibers comprise carded fibers.

18. The absorbent article of claim 14, wherein the fibers comprise continuous fibers.

19. The absorbent article of claim 14, wherein the increased permeability regions have a second basis weight in the range of less than 60% to less than 35% of the first basis weight of the land areas, according to the Micro-CT Test.

20. The absorbent article of claim 14, wherein, in the three-dimensional elements, the nonwoven material has a third basis weight, and wherein the third basis weight is substantially the same as the first basis weight of the land areas, according to the Micro-CT Test.

* * * * *